(12) United States Patent
Joncour Genicot et al.

(10) Patent No.: US 8,420,355 B2
(45) Date of Patent: Apr. 16, 2013

(54) 4S-IOTA-CARRAGEENAN SULFATASE AND USE THEREOF TO OBTAIN ALPHA-CARRAGEENAN

(75) Inventors: Sabine Joncour Genicot, Saint Pol de Leon (FR); William Helbert, Roscoff (FR)

(73) Assignees: Centre National de la Recherche (CNRS), Paris (FR); Universite Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 13/265,795

(22) PCT Filed: Apr. 22, 2010

(86) PCT No.: PCT/EP2010/055395
§ 371 (c)(1),
(2), (4) Date: Oct. 21, 2011

(87) PCT Pub. No.: WO2010/122127
PCT Pub. Date: Oct. 28, 2010

(65) Prior Publication Data
US 2012/0052533 A1 Mar. 1, 2012

(30) Foreign Application Priority Data
Apr. 22, 2009 (FR) ..................... 09 52642

(51) Int. Cl.
*C12P 19/04* (2006.01)
*C12N 9/16* (2006.01)
*C12N 15/00* (2006.01)
*C12N 5/02* (2006.01)
*C12N 5/04* (2006.01)
*C12N 1/20* (2006.01)
*C12N 1/00* (2006.01)
*C12Q 1/48* (2006.01)
*C07K 1/14* (2006.01)

(52) U.S. Cl.
USPC .......... 435/101; 435/196; 435/320.1; 435/15; 435/325; 435/419; 435/252.3; 435/254.11; 530/412

(58) Field of Classification Search .................. None
See application file for complete search history.

(56) References Cited

PUBLICATIONS

McLean et al., Eur. J. Biochem. 101:497-505, 1979.*
Zinoun et al., "Evidence of Sulfohydrolase Activity in the Red Alga *Calliblepharis jubata*," Botanica Marina, vol. 40, pp. 49-53, Jan. 1, 1997.
Zablackis et al., "The Carrageenan of *Catenella nipae* Zanard., a Marine Red Alga," Botanica Marina, vol. 29, pp. 319-322, 1986.
Wong et al., "Sulfohydrolase Activity and Carrageenan Biosynthesis in *Chondrus crispus* (Rhodophyceae)," Plant Physiol. vol. 61, pp. 663-666, 1978.
Potin et al., "Purification and characterization of a new k-carrageenase from a marine *Cytophaga*-like bacterium," Eur. J. Biochem., vol. 201, pp. 241-247, 1991.
Michel et al., "Bioconversion of red seaweed galactans: a focus on bacterial agarases and carrageenases," Appl. Microbiol. Biotechnol., vol. 71, pp. 23-33, 2006.
Genicot-Joncour et al., "The Cyclization of the 3,6-Anhydro-Galctose Ring of t-Carrageenan is Catalyzed by Two D-Galactose-2,6-Sulfurylases in the Red Alga *Chondrus crispus*," Plant Physiology, vol. 151, pp. 1609-1616, Nov. 2009.
Falshaw et al., "Structural analysis of carrageenans from Burmese and Thai samples of *Catenella nipae* Zanardini," Carbohydrate Research, vol. 285, pp. 81-98, 1996.
Database UniProt (Online), "SubName: Full=Putative uncharacterized protein;" XP002562258, extrait de EBI accession No. UNIPROT: Q3IKL4, Database accession No. Q3IKL4, Nov. 8, 2005.
International Search Report issued for application No. PCT/EP2010/055395 on Oct. 5, 2010.
French Search Report issued for application No. FR 0952642 on Jan. 13, 2010.

* cited by examiner

*Primary Examiner* — David J Steadman
(74) *Attorney, Agent, or Firm* — Foley & Lardner LLP

(57) ABSTRACT

The present invention relates to 4S-iota-carrageenan sulfatase and to the use thereof for partially or totally converting the iota-carrageenan into iota-/alpha-carrageenan or alpha-carrageenan. The invention also relates to the method for extracting said enzyme from a *Pseudoalteromonas* bacteria population or from red marine algae. Finally, the present invention relates to the use of 4S-iota-carrageenan sulfatase to prepare a texturizing agent containing alpha-carrageenan.

13 Claims, 3 Drawing Sheets

Figure 1:
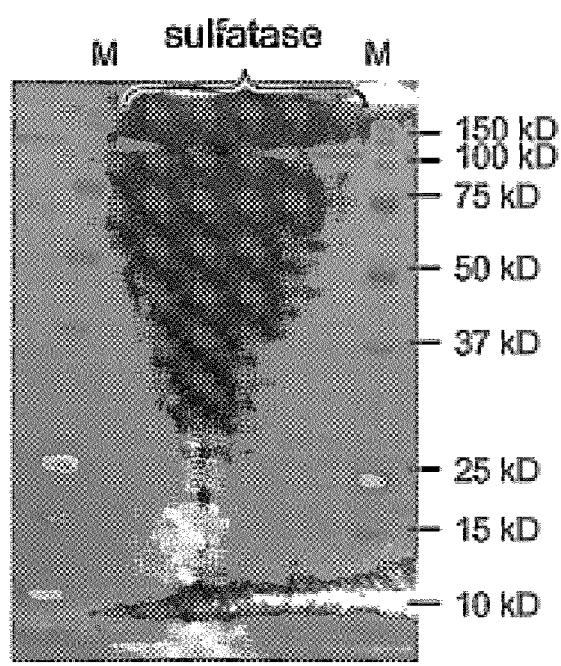

MKKMLQTVLALSVSLALGNAQAQQDDEPKWQVDSPKGQFVDATISVDQGTWMNLDISPDG
KTLVFDLLGDIYTMPISGGNATQLTSDIAWQMQPRFSPNGKHIAFTSDQGGGDNIWIMDL
NGENQSAVTDETFFLLNSPAWSPDGDYLVARKHFTASFSLGAGEVWLYHKAGGKGVQLTK
RADDQKDLGEPMFSPDGRYVYFSHDATPGKTFHYSKDSVAGIYKIKRYDRETGEIETVIS
GNGGAIRPTPSPDGKKLAYIKRDDFQFSLYLYDLTSGEHTKLYDKLERDNQETWAIHGVY
PTIANTPDNQQLVFWAGGTIHKLDVSDKSVETIAFKVQTTKKIQKAVRFTQNLDTDEFDV
KMLRNVQISPDGETAIFEALGHIYKRDLESGKIKRLTKQTDHYELFAQYSRDGKKIVYTT
WDDNEQGQVRVVSASSGRGDTITEQPGKTVEDTFSPDGRTVVYRKATGGSILNPKWSLNP
GVYSVSTKGGKSELISKNGYQPQFGAANDRVYIMSPWPKPTLSVVELDTKKVRKLYESEH
ATEFRVSPDGQYLAFAERFKVFVTPEVENGKTLNISPTDNQFPIEQLSVRAGENISWSAN
SNKLYWTLGPELYHASLEGMFAINKADDKDFKVKSGDNISFSKRMAEPKGMIALTGAKII
TMDGEKVIENGVIITDGKHIKAIGTAAEVSIPKGAKVVDVTGKTIMPGIVDAHAHGSQAS
DEIIPQQNWKNFAGLALGVTTIHDPSNDTSEIFTASEMQKAGMIVGPRIFSTGTILYGAN
MPGYTSHIDSLDDAKFHLERLKKVGAFSVKSYNQPRREQRQQVIEAGRELQMMVVPEGGS
LLQHNLSMIVDGHTGIEHSIPVEHIYDDIKQLWSQSDVGYTPTLVVAYGGINGENYWYDK
TDVWNHPRLSKFVPKNQLLPRSMRRVKAPEHHYNHFNNARVAAELQDLGVLVNLGAHGQR
EGLGAHWEMRMFAQGGNTPLEAIRASTLDPAKYLGLDKNVGSLEVGKLADLMVIDGDPLS
NIRDSDKIDYTMINGRLFNAATMVEVGKRQRKPLYFENNK

Figure 2

SEQUENCE LISTING

<160> NUMBER OF SEQ ID NOS: 9

<210> SEQ ID NO 1
<211> LENGTH: 3114
<212> TYPE: DNA
<213> ORGANISM: Pseudoalteromonas haloplanktis
<220> FEATURE:
<221> NAME/KEY: misc_feature
<223> OTHER INFORMATION: 4S-iota-carraghenane sulfatase

<400> SEQUENCE: 1

```
caacaagacg atgagccaaa atggcaagta gattcaccta aagggcaatt tgttgatgca      60
tctattagtg tagagcaagg cacatggatg aatgtcgata taagtcctga cggagaaacc     120
ttagtatttg atttactggg cgatatttac accatgccaa tgagtggtgg taaagcgact     180
aaaataacct cagacattgc atggcaaatg cagccgcgct ttagcccaga tggcaagcac     240
attgctttta catcagatca aggcggtggt gacaatattt ggataatgga tgttaacggc     300
gaaaaccaaa ccgccgtcac tgacgaaaca tttagattac tcaatagccc tgcgtggagc     360
cctgatggtg attatttagt tgcacgtaag cattttaccg ccagtcgctc gctaggtgcg     420
ggtgaagttt ggctttatca caaagccggc ggtaaagggg tgcaactgac taaacgtgaa     480
aacgatcaaa aagactttagg tgaacccatg ttttcaccgg atggtcggta tgtttatttt     540
tctcacgatg caaccccagg taaaactttt cattattcaa aagactctgt tgccggtatt     600
tataaaatta gcgttatga ccgtgaaaca ggcgacatag aaaccattat aagtggcatg     660
ggcggggcaa taagaccgac gccgtcgcca gatggtaaaa aactagcgta cataaagcgt     720
gatgactttc aaaccagcct gtacttatat gatttaacca gtggtgagca tactaagcta     780
tacgacaagc tagagcgcga tatgcaagaa acgtgggcga ttcatggcgt atatccgact     840
attgcgtgga ccccagataa cgaagagctg gtattttggg ctggtggcac ccttcataaa     900
tttaatgtag ataataaatc agtcagcgat attgcattta agtagacac tacgaaaaaa     960 attcaaaaag cagtgcgttt tactcaaaat atcgacactg atgagtttga tgtaaaaatg    1020
ctgcgtaatg tgcaaattag ccctgacggt gaaaccgcac tttttgaagc attgggctat    1080
atttacatgc gcgacttaga atcaggaaaa ataaagcgct taactaagca aaccgatcat    1140
tatgagttat tcccgcagta ttctcgtgat ggcaaaaaca ttgtctacac cacgtgggat    1200
gataatgaac aaggcaccgt gcgtgtcgtc tctgcacgca gtggtcgggg cgacactatt    1260
acacaagagc cgggaaaata cgtagagcca acatttagtc cagacggcaa accgtggtg    1320 tatcgtaaag ccagcggcgg caacatttta aaccctaagt ggtcactgca tcctggggta    1380
tacagtgtta gtgctaaagg cggaaaaagt gagctcattt ctaaaagtgg ctatcaacct    1440
cagtttggca gtgccaacga tcgtgtttat attatgagcc catggcctaa gccgacatta    1500
agtgtggtag agcttgaaag taaaaaagta cgtaaactgt atgaatcaga gcacgccact    1560
gaatttagag tctctcctga tggtgagtat ttagcttttg ctgagcgctt taaagtactt    1620
gttactccat ttgtagagcg cggcaaaacg ataaatattg ggcccaaaga cagtcaattt    1680
ccaattgagc agctatctgt acgcgccggt gaaaacatta gctggagtgc aaacagcaat    1740
aaactgtatt ggacactggg gcctgagctt taccatgcca gtttagaggg gatgtttgcg    1800
attaataaag cggatgataa agacgttaaa gtaaaaagcg ggactaacat cggctttagt    1860
aaaaaaatgg ctgaaccgca gggcatgatt gcattaactg cgctaaaat tattaccatg    1920 gagggtgaaa aggtcattga aaatggcgtt attgttaccg atggcaaaca tatcaaagcc    1980
```

-continued

```
attggcactg ctgctgatgt gagcattcct aagggagcaa aggtcattga tgtaacaggt      2040
aaaacaatta tgccaggcat tgtagatgcc catgctcatg gctcacaagc cagtgatgaa      2100
attatcccgc agcaaaattg gaaaaactta gcaggtcttg cgctgggtgt tactactatt      2160
cacgacccat caaacgatac cactgaaata tttaccgcga gtgaaatgca aaaagcgggg      2220
atgatcgttg gtccgcgtat tttctctacc ggtactattt tatacggtgc gaatatgcct      2280
gggtatacct cgcatattga ctcattagat gatgctaaat ttcatttaga gcgtcttaaa      2340
aaagtgggtg cgtttagtgt taaatcctat aaccaaccgc gcagagagca gcgtcagcaa      2400
gttatagaag cagggcgaat gcttgaaatg atggtagtcc ctgaagggg gtcattatta      2460 caacataact tgagcatggt agtcgatggt catacaggta ttgaacattc aattcctgtt      2520
gaacatattt atgacgatat taagcagcta tggtcacaaa gtgatgtagg ttacacacct      2580
acattggtgg ttgcctatgg cggtatttgg ggtgaaaact actggtatga taaaacggac      2640
gtatggaatc atccacgttt aagtaaattt gtgcctaaaa accaattatt accgcgctca      2700
atgcgccgag ttaaagcacc cgatcatcac tataatcact ttaacaatgc tcgcgtagcg      2760
gctgagttac aagatttagg tgtacttgtt aatttgggtg cgcatggcca acgtgagggg      2820
ttaggtgcgc attgggaaat gtggatgttt gcccaaggcg gcatgacgtc actggaagca      2880
attagagcat ctacactcga tccggcaaaa tatttaggcc tagataaaaa tgtgggttca      2940
ttagaggtcg gtaaactggc agatttaatg gttattgatg gcgacccact gaaaaacatt      3000
cgtgattcag acaaaattga ttacaccatg atcaacggcc gtttgttcga cgcagctacc      3060
atgaacgaag tgggtaaaaa acagcgtaaa ccactttatt ttgaaaacaa caaa            3114
```

<210> SEQ ID NO 2
<211> LENGTH: 1038
<212> TYPE: PRT
<213> ORGANISM: Pseudoalteromonas haloplanktis
<220> FEATURE:
<221> NAME/KEY: misc_feature
<223> OTHER INFORMATION: 4S-iota-carraghenane sulfatase

<400> SEQUENCE: 2

```
Gln Gln Asp Asp Glu Pro Lys Trp Gln Val Asp Ser Pro Lys Gly Gln
1               5                   10                  15

Phe Val Asp Ala Ser Ile Ser Val Glu Gln Gly Thr Trp Met Asn Val
            20                  25                  30

Asp Ile Ser Pro Asp Gly Glu Thr Leu Val Phe Asp Leu Leu Gly Asp
        35                  40                  45

Ile Tyr Thr Met Pro Met Ser Gly Gly Lys Ala Thr Lys Ile Thr Ser
    50                  55                  60

Asp Ile Ala Trp Gln Met Gln Pro Arg Phe Ser Pro Asp Gly Lys His
65                  70                  75                  80

Ile Ala Phe Thr Ser Asp Gln Gly Gly Gly Asp Asn Ile Trp Ile Met
                85                  90                  95

Asp Val Asn Gly Glu Asn Gln Thr Ala Val Thr Asp Glu Thr Phe Arg
            100                 105                 110

Leu Leu Asn Ser Pro Ala Trp Ser Pro Asp Gly Asp Tyr Leu Val Ala
        115                 120                 125

Arg Lys His Phe Thr Ala Ser Arg Ser Leu Gly Ala Gly Glu Val Trp
    130                 135                 140

Leu Tyr His Lys Ala Gly Gly Lys Gly Val Gln Leu Thr Lys Arg Glu
145                 150                 155                 160
```

```
Asn Asp Gln Lys Asp Leu Gly Glu Pro Met Phe Ser Pro Asp Gly Arg
            165                 170                 175

Tyr Val Tyr Phe Ser His Asp Ala Thr Pro Gly Lys Thr Phe His Tyr
        180                 185                 190

Ser Lys Asp Ser Val Ala Gly Ile Tyr Lys Ile Lys Arg Tyr Asp Arg
        195                 200                 205

Glu Thr Gly Asp Ile Glu Thr Ile Ile Ser Gly Met Gly Gly Ala Ile
    210                 215                 220

Arg Pro Thr Pro Ser Pro Asp Gly Lys Lys Leu Ala Tyr Ile Lys Arg
225                 230                 235                 240

Asp Asp Phe Gln Thr Ser Leu Tyr Leu Tyr Asp Leu Thr Ser Gly Glu
            245                 250                 255

His Thr Lys Leu Tyr Asp Lys Leu Glu Arg Asp Met Gln Glu Thr Trp
        260                 265                 270

Ala Ile His Gly Val Tyr Pro Thr Ile Ala Trp Thr Pro Asp Asn Glu
        275                 280                 285

Glu Leu Val Phe Trp Ala Gly Gly Thr Leu His Lys Phe Asn Val Asp
    290                 295                 300

Asn Lys Ser Val Ser Asp Ile Ala Phe Lys Val Asp Thr Thr Lys Lys
305                 310                 315                 320

Ile Gln Lys Ala Val Arg Phe Thr Gln Asn Ile Asp Thr Asp Glu Phe
            325                 330                 335

Asp Val Lys Met Leu Arg Asn Val Gln Ile Ser Pro Asp Gly Glu Thr
        340                 345                 350

Ala Leu Phe Glu Ala Leu Gly Tyr Ile Tyr Met Arg Asp Leu Glu Ser
        355                 360                 365

Gly Lys Ile Lys Arg Leu Thr Lys Gln Thr Asp His Tyr Glu Leu Phe
    370                 375                 380

Pro Gln Tyr Ser Arg Asp Gly Lys Asn Ile Val Tyr Thr Thr Trp Asp
385                 390                 395                 400

Asp Asn Glu Gln Gly Thr Val Arg Val Val Ser Ala Arg Ser Gly Arg
            405                 410                 415

Gly Asp Thr Ile Thr Gln Glu Pro Gly Lys Tyr Val Gly Pro Thr Phe
        420                 425                 430

Ser Pro Asp Gly Lys Thr Val Val Tyr Arg Lys Ala Ser Gly Gly Asn
        435                 440                 445

Ile Leu Asn Pro Lys Trp Ser Leu His Pro Gly Val Tyr Ser Val Ser
    450                 455                 460

Ala Lys Gly Gly Lys Ser Gly Leu Ile Ser Lys Ser Gly Tyr Gln Pro
465                 470                 475                 480

Gln Phe Gly Ser Ala Asn Asp Arg Val Tyr Ile Met Ser Pro Trp Pro
            485                 490                 495

Lys Pro Thr Leu Ser Val Val Glu Leu Glu Ser Lys Lys Val Arg Lys
        500                 505                 510

Leu Tyr Glu Ser Glu His Ala Thr Glu Phe Arg Val Ser Pro Asp Gly
        515                 520                 525

Glu Tyr Leu Ala Phe Ala Glu Arg Phe Lys Val Leu Thr Pro Phe
    530                 535                 540

Val Glu Arg Gly Lys Thr Ile Asn Ile Gly Pro Lys Asp Ser Gln Phe
545                 550                 555                 560

Pro Ile Glu Gln Leu Ser Val Arg Ala Gly Glu Asn Ile Ser Trp Ser
            565                 570                 575

Ala Asn Ser Asn Lys Leu Tyr Trp Thr Leu Gly Pro Glu Leu Tyr His
        580                 585                 590
```

```
Ala Ser Leu Glu Gly Met Phe Ala Ile Asn Lys Ala Asp Asp Lys Asp
        595                 600                 605
Val Lys Val Lys Ser Gly Thr Asn Ile Gly Phe Ser Lys Lys Met Ala
610                 615                 620
Glu Pro Gln Gly Met Ile Ala Leu Thr Gly Ala Lys Ile Ile Thr Met
625                 630                 635                 640
Glu Gly Glu Lys Val Ile Glu Asn Gly Val Ile Val Thr Asp Gly Lys
                645                 650                 655
His Ile Lys Ala Ile Gly Thr Ala Ala Asp Val Ser Ile Pro Lys Gly
                660                 665                 670
Ala Lys Val Ile Asp Val Thr Gly Lys Thr Ile Met Pro Gly Ile Val
            675                 680                 685
Asp Ala His Ala His Gly Ser Gln Ala Ser Asp Glu Ile Ile Pro Gln
        690                 695                 700
Gln Asn Trp Lys Asn Leu Ala Gly Leu Ala Leu Gly Val Thr Thr Ile
705                 710                 715                 720
His Asp Pro Ser Asn Asp Thr Thr Glu Ile Phe Thr Ala Ser Glu Met
                725                 730                 735
Gln Lys Ala Gly Met Ile Val Gly Pro Arg Ile Phe Ser Thr Gly Thr
                740                 745                 750
Ile Leu Tyr Gly Ala Asn Met Pro Gly Tyr Thr Ser His Ile Asp Ser
            755                 760                 765
Leu Asp Asp Ala Lys Phe His Leu Glu Arg Leu Lys Lys Val Gly Ala
        770                 775                 780
Phe Ser Val Lys Ser Tyr Asn Gln Pro Arg Arg Glu Gln Arg Gln Gln
785                 790                 795                 800
Val Ile Glu Ala Gly Arg Met Leu Glu Met Met Val Val Pro Glu Gly
                805                 810                 815
Gly Ser Leu Leu Gln His Asn Leu Ser Met Val Val Asp Gly His Thr
            820                 825                 830
Gly Ile Glu His Ser Ile Pro Val Glu His Ile Tyr Asp Asp Ile Lys
        835                 840                 845
Gln Leu Trp Ser Gln Ser Asp Val Gly Tyr Thr Pro Thr Leu Val Val
    850                 855                 860
Ala Tyr Gly Gly Ile Trp Gly Glu Asn Tyr Trp Tyr Asp Lys Thr Asp
865                 870                 875                 880
Val Trp Asn His Pro Arg Leu Ser Lys Phe Val Pro Lys Asn Gln Leu
                885                 890                 895
Leu Pro Arg Ser Met Arg Val Lys Ala Pro Asp His His Tyr Asn
            900                 905                 910
His Phe Asn Asn Ala Arg Val Ala Ala Glu Leu Gln Asp Leu Gly Val
        915                 920                 925
Leu Val Asn Leu Gly Ala His Gly Gln Arg Glu Gly Leu Gly Ala His
    930                 935                 940
Trp Glu Met Trp Met Phe Ala Gln Gly Gly Met Thr Ser Leu Glu Ala
945                 950                 955                 960
Ile Arg Ala Ser Thr Leu Asp Pro Ala Lys Tyr Leu Gly Leu Asp Lys
                965                 970                 975
Asn Val Gly Ser Leu Glu Val Gly Lys Leu Ala Asp Leu Met Val Ile
            980                 985                 990
Asp Gly Asp Pro Leu Lys Asn Ile Arg Asp Ser Asp Lys Ile Asp Tyr
        995                 1000                1005
Thr Met Ile Asn Gly Arg Leu Phe Asp Ala Ala Thr Met Asn Glu
```

| | | | |
|---|---|---|---|
| 1010 | | 1015 | 1020 |

Val Gly Lys Lys Gln Arg Lys Pro Leu Tyr Phe Glu Asn Asn Lys
　　1025　　　　　　　1030　　　　　　　1035

<210> SEQ ID NO 3
<211> LENGTH: 3114
<212> TYPE: DNA
<213> ORGANISM: Pseudoalteromonas carrageenovera
<220> FEATURE:
<221> NAME/KEY: misc_feature
<223> OTHER INFORMATION: 4S-iota-carraghenane sulfatase

<400> SEQUENCE: 3

| | | | | | |
|---|---|---|---|---|---|
| caacaagacg | atgagccaaa | atggcaagta | gattcaccta | aaggccagtt | tgttgacgct | 60 |
| gcaattagcg | ttgaacaagg | cacatggatg | aatattgatg | taagccctga | tggaaaaaca | 120 |
| gttgtgtttg | acctgctcgg | tgatatttat | acaatgccaa | tgagtggcgg | tacagctaca | 180 |
| aaacttacct | cagatattgc | atggcagatg | cagcctcgct | ttagtccaaa | tggaaaacac | 240 |
| attgctttta | cctcagatca | ggggggtggc | gataatattt | ggataatgga | tttaaatggc | 300 |
| gaaaaccaac | acgcggttac | tgatgaaacc | tttaggcttt | taaacagccc | cgcatggagc | 360 |
| cctgatggcg | attacctagt | tgcacgtaag | cactttactg | caagccgctc | gttgggagct | 420 |
| ggtgaagtgt | ggctttatca | taaggcgggt | ggtaaaggtg | ttcagcttac | taagcgcgag | 480 |
| aacgatcaaa | aagatttagg | tgagccaatg | ttctccccag | atggacgtta | tgtttacttc | 540 |
| tcacatgatg | caacgccagg | taaaactttt | cattattcaa | aagattcagt | agccggtatt | 600 |
| tataaaatta | aacgctacga | ccgtgaaacg | ggcgagatag | aaactgttat | tgacactatg | 660 |
| gggggagcga | taaggcccac | accgtcgccc | gatggcaaaa | agttagcgta | cattaagcgc | 720 |
| gatgactttc | aaaccagcct | ttatttatac | gatttaagca | gcggcgagca | cactaagctt | 780 |
| tacgataaac | ttgagcgtga | catgcaagaa | acgtgggcaa | ttcatggtgt | ttatccaacc | 840 |
| attgcatgga | cgccagataa | tgaagagctg | gtattttggg | ctggtggtac | tattcacaag | 900 |
| ctagatgttg | cagacaaatc | tgttaaaacc | atacctttta | aagtgcaaac | aagtaaaaaa | 960 |
| attcaaaaag | cagtgcgatt | tacacaaaat | ttagacaccg | acgagtttga | tgtaaaaatg | 1020 |
| ctgcgaaatg | tacaggtaag | cccagatggc | gcaacggcta | tttttgaagc | acttggttat | 1080 |
| atttataaac | gtgatttaga | gtcgggtaag | attaaacgtt | taactaaaca | aactgagcat | 1140 |
| tatgagttat | tcccgcaata | ctctcgtgat | ggtaaaaaaa | tcgtatacac | cacttggaac | 1200 |
| gataacaagc | aaggcacggt | acgtgttgta | tcgtcgcgca | gcggacgtgg | cgataccatt | 1260 |
| accacagagc | ctggcaagta | tgtagagcca | acatttagcc | caaatggtaa | aacggttgtg | 1320 |
| taccgaaaag | ccacaggtgg | cagcatatta | aaccctaagt | ggtctttaaa | cccaggcatt | 1380 |
| tatagcgtaa | gcgttaaagg | tggtaaaagt | gagctgattt | ctaaaagcgg | gtatcaacca | 1440 |
| cagtttggtg | atgaaagtga | tcgcgttttt | attatgagcc | catggccaaa | accaacgctt | 1500 |
| agcgtagtag | atcttaaaag | taaaaaaata | cgtaagcttt | atgagtctga | gcatgcaact | 1560 |
| gaatttagag | tttcaccaga | tggtcaatat | ttagcgtttg | ctgagcggtt | taaagtgttt | 1620 |
| gtaacacctt | ttgtagaaag | tggctcaaca | attaatataa | gccctaagga | tagccagttc | 1680 |
| cctatagagc | aattgtctgc | tcgtgcgggt | gaaaacatta | gctggaatac | taaaagcaat | 1740 |
| acgctttatt | ggactttagg | cccagagctt | taccatgcaa | gtttagaggg | aatgtttgca | 1800 |
| attaataaag | ccgatgatgc | tgactttaaa | gtaaaaagtg | gcgataacat | cggttttagt | 1860 |
| aaaaaaatgg | ctaagcctaa | aggcatgatt | gcgttaaaag | gcgcaaaaat | tattaccatg | 1920 |

```
gatggcgaaa aggtcattga aaatggtgtg ataattacag atggcaagca catcaaatca    1980
attggtacag ctaatgaagt aaccatacca aaagatgcaa aagtaattga tgtaacaggt    2040
aaaacgatta tgcctggtat tgttgatgca catgcacatg gctctcaagc aagtgatgaa    2100
ataattccac agcaaaattg gaaaaacttt gcaggtttag cgctgggtgt cactacaatt    2160
catgacccat caaatgatac aacagaaata tttactgcca gtgaaatgca aaaggcaggg    2220
atgattgttg gcccgcgtat tttctctaca gggaccattt tatatggcgc aaatatgccg    2280
ggttatacgt cacacataga ttcgttagag gatgctaaat ttcatttaga gcgacttaaa    2340
aaagtggggg cgtttagtgt taaatcgtat aaccaaccac ggcgtgagca gcgccagcaa    2400
gtaattgaag ccgggcgtga actggaaatg atggtagtgc agaaggtgg ctcattattg     2460 caacataact taagtatggt ggttgatggc cacacaggta ttgaacattc tattcctgtt    2520
gaacatattt acgatgatat aaagcagtta tggtcacaaa gtgatgtagg ctatacacct    2580
acattagttg ttgcttacgg tggtatatgg ggtgaaaact attggtatga taaaacggat    2640
gtgtggaacc acccacgttt aagtaaattt gtgcctaaaa atcaattatt accgcgctct    2700
atgcgccgcg taaaagcgcc tgatcatcac tataatcact ttaataatgc acgtgtggca    2760
aaagagctgc aagacttggg cgtactggtt aatttaggtg cccatgggca gcgtgaaggg    2820
cttggagcac attgggaaat gtggatgttc gctcaaggcg aatgagctc actgaggct     2880 attagagcat caacgctcga cccagccaaa tatttagggc ttgataaaaa cgtaggctcg    2940
cttgaagtag gtaaacttgc cgatttaatg gtaatagatg gcaatccact taaaatatt    3000 cgagattcgg ataaagttga ttacaccatg atcaatggtc gtttatttga tgcaagtaca    3060
atgaatgaag tgggtaaaaa acagcgtaaa ccactttatt ttgaaaacaa caaa          3114
```

<210> SEQ ID NO 4
<211> LENGTH: 1038
<212> TYPE: PRT
<213> ORGANISM: Pseudoalteromonas carrageenovera
<220> FEATURE:
<221> NAME/KEY: misc_feature
<223> OTHER INFORMATION: 4S-iota-carraghenane sulfatase

<400> SEQUENCE: 4

```
Gln Gln Asp Asp Glu Pro Lys Trp Gln Val Asp Ser Pro Lys Gly Gln
1               5                   10                  15

Phe Val Asp Ala Ala Ile Ser Val Glu Gln Gly Thr Trp Met Asn Ile
            20                  25                  30

Asp Val Ser Pro Asp Gly Lys Thr Val Val Phe Asp Leu Leu Gly Asp
        35                  40                  45

Ile Tyr Thr Met Pro Met Ser Gly Gly Thr Ala Thr Lys Leu Thr Ser
    50                  55                  60

Asp Ile Ala Trp Gln Met Gln Pro Arg Phe Ser Pro Asn Gly Lys His
65                  70                  75                  80

Ile Ala Phe Thr Ser Asp Gln Gly Gly Gly Asp Asn Ile Trp Ile Met
                85                  90                  95

Asp Leu Asn Gly Glu Asn Gln His Ala Val Thr Asp Glu Thr Phe Arg
            100                 105                 110

Leu Leu Asn Ser Pro Ala Trp Ser Pro Asp Gly Asp Tyr Leu Val Ala
        115                 120                 125

Arg Lys His Phe Thr Ala Ser Arg Ser Leu Gly Ala Gly Glu Val Trp
    130                 135                 140

Leu Tyr His Lys Ala Gly Gly Lys Gly Val Gln Leu Thr Lys Arg Glu
145                 150                 155                 160
```

```
Asn Asp Gln Lys Asp Leu Gly Glu Pro Met Phe Ser Pro Asp Gly Arg
            165                 170                 175

Tyr Val Tyr Phe Ser His Asp Ala Thr Pro Gly Lys Thr Phe His Tyr
            180                 185                 190

Ser Lys Asp Ser Val Ala Gly Ile Tyr Lys Ile Lys Arg Tyr Asp Arg
            195                 200                 205

Glu Thr Gly Glu Ile Glu Thr Val Ile Asp Thr Met Gly Gly Ala Ile
            210                 215                 220

Arg Pro Thr Pro Ser Pro Asp Gly Lys Lys Leu Ala Tyr Ile Lys Arg
225                 230                 235                 240

Asp Asp Phe Gln Thr Ser Leu Tyr Leu Tyr Asp Leu Ser Ser Gly Glu
            245                 250                 255

His Thr Lys Leu Tyr Asp Lys Leu Glu Arg Asp Met Gln Glu Thr Trp
            260                 265                 270

Ala Ile His Gly Val Tyr Pro Thr Ile Ala Trp Thr Pro Asp Asn Glu
            275                 280                 285

Glu Leu Val Phe Trp Ala Gly Gly Thr Ile His Lys Leu Asp Val Ala
            290                 295                 300

Asp Lys Ser Val Lys Thr Ile Pro Phe Lys Val Gln Thr Ser Lys Lys
305                 310                 315                 320

Ile Gln Lys Ala Val Arg Phe Thr Gln Asn Leu Asp Thr Asp Glu Phe
            325                 330                 335

Asp Val Lys Met Leu Arg Asn Val Gln Val Ser Pro Asp Gly Ala Thr
            340                 345                 350

Ala Ile Phe Glu Ala Leu Gly Tyr Ile Tyr Lys Arg Asp Leu Glu Ser
            355                 360                 365

Gly Lys Ile Lys Arg Leu Thr Lys Gln Thr Glu His Tyr Glu Leu Phe
            370                 375                 380

Pro Gln Tyr Ser Arg Asp Gly Lys Lys Ile Val Tyr Thr Thr Trp Asn
385                 390                 395                 400

Asp Asn Lys Gln Gly Thr Val Arg Val Val Ser Ser Arg Ser Gly Arg
            405                 410                 415

Gly Asp Thr Ile Thr Thr Glu Pro Gly Lys Tyr Val Glu Pro Thr Phe
            420                 425                 430

Ser Pro Asn Gly Lys Thr Val Val Tyr Arg Lys Ala Thr Gly Gly Ser
            435                 440                 445

Ile Leu Asn Pro Lys Trp Ser Leu Asn Pro Gly Ile Tyr Ser Val Ser
450                 455                 460

Val Lys Gly Gly Lys Ser Glu Leu Ile Ser Lys Ser Gly Tyr Gln Pro
465                 470                 475                 480

Gln Phe Gly Asp Glu Ser Asp Arg Val Phe Ile Met Ser Pro Trp Pro
            485                 490                 495

Lys Pro Thr Leu Ser Val Val Asp Leu Lys Ser Lys Lys Ile Arg Lys
            500                 505                 510

Leu Tyr Glu Ser Glu His Ala Thr Glu Phe Arg Val Ser Pro Asp Gly
            515                 520                 525

Gln Tyr Leu Ala Phe Ala Glu Arg Phe Lys Val Phe Val Thr Pro Phe
            530                 535                 540

Val Glu Ser Gly Ser Thr Ile Asn Ile Ser Pro Lys Asp Ser Gln Phe
545                 550                 555                 560

Pro Ile Glu Gln Leu Ser Ala Arg Ala Gly Glu Asn Ile Ser Trp Asn
            565                 570                 575

Thr Lys Ser Asn Thr Leu Tyr Trp Thr Leu Gly Pro Glu Leu Tyr His
```

-continued

```
            580                 585                 590
Ala Ser Leu Glu Gly Met Phe Ala Ile Asn Lys Ala Asp Asp Ala Asp
        595                 600                 605

Phe Lys Val Lys Ser Gly Asp Asn Ile Gly Phe Ser Lys Lys Met Ala
610                 615                 620

Lys Pro Lys Gly Met Ile Ala Leu Lys Gly Ala Lys Ile Ile Thr Met
625                 630                 635                 640

Asp Gly Glu Lys Val Ile Glu Asn Gly Val Ile Ile Thr Asp Gly Lys
                645                 650                 655

His Ile Lys Ser Ile Gly Thr Ala Asn Glu Val Thr Ile Pro Lys Asp
                660                 665                 670

Ala Lys Val Ile Asp Val Thr Gly Lys Thr Ile Met Pro Gly Ile Val
                675                 680                 685

Asp Ala His Ala His Gly Ser Gln Ala Ser Asp Glu Ile Ile Pro Gln
    690                 695                 700

Gln Asn Trp Lys Asn Phe Ala Gly Leu Ala Leu Gly Val Thr Thr Ile
705                 710                 715                 720

His Asp Pro Ser Asn Asp Thr Thr Glu Ile Phe Thr Ala Ser Glu Met
                725                 730                 735

Gln Lys Ala Gly Met Ile Val Gly Pro Arg Ile Phe Ser Thr Gly Thr
                740                 745                 750

Ile Leu Tyr Gly Ala Asn Met Pro Gly Tyr Thr Ser His Ile Asp Ser
        755                 760                 765

Leu Glu Asp Ala Lys Phe His Leu Glu Arg Leu Lys Lys Val Gly Ala
    770                 775                 780

Phe Ser Val Lys Ser Tyr Asn Gln Pro Arg Arg Glu Gln Arg Gln Gln
785                 790                 795                 800

Val Ile Glu Ala Gly Arg Glu Leu Glu Met Met Val Val Pro Glu Gly
                805                 810                 815

Gly Ser Leu Leu Gln His Asn Leu Ser Met Val Val Asp Gly His Thr
        820                 825                 830

Gly Ile Glu His Ser Ile Pro Val Glu His Ile Tyr Asp Asp Ile Lys
        835                 840                 845

Gln Leu Trp Ser Gln Ser Asp Val Gly Tyr Thr Pro Thr Leu Val Val
    850                 855                 860

Ala Tyr Gly Gly Ile Trp Gly Glu Asn Tyr Trp Tyr Asp Lys Thr Asp
865                 870                 875                 880

Val Trp Asn His Pro Arg Leu Ser Lys Phe Val Pro Lys Asn Gln Leu
                885                 890                 895

Leu Pro Arg Ser Met Arg Arg Val Lys Ala Pro Asp His His Tyr Asn
                900                 905                 910

His Phe Asn Asn Ala Arg Val Ala Lys Glu Leu Gln Asp Leu Gly Val
        915                 920                 925

Leu Val Asn Leu Gly Ala His Gly Gln Arg Glu Gly Leu Gly Ala His
    930                 935                 940

Trp Glu Met Trp Met Phe Ala Gln Gly Gly Met Ser Ser Leu Glu Ala
945                 950                 955                 960

Ile Arg Ala Ser Thr Leu Asp Pro Ala Lys Tyr Leu Gly Leu Asp Lys
                965                 970                 975

Asn Val Gly Ser Leu Glu Val Gly Lys Leu Ala Asp Leu Met Val Ile
        980                 985                 990

Asp Gly Asn Pro Leu Lys Asn Ile Arg Asp Ser Asp Lys Val Asp Tyr
    995                 1000                1005
```

```
Thr Met Ile Asn Gly Arg Leu Phe Asp Ala Ser Thr Met Asn Glu
    1010                1015                1020

Val Gly Lys Lys Gln Arg Lys Pro Leu Tyr Phe Glu Asn Asn Lys
    1025                1030                1035

<210> SEQ ID NO 5
<211> LENGTH: 1060
<212> TYPE: PRT
<213> ORGANISM: Pseudoalteromonas haloplanktis
<220> FEATURE:
<221> NAME/KEY: misc_feature
<223> OTHER INFORMATION: Q3IKL4

<400> SEQUENCE: 5

Met Lys Lys Met Leu Gln Thr Val Leu Ala Leu Ser Val Ser Leu Ala
1               5                   10                  15

Leu Gly Asn Ala Gln Ala Gln Gln Asp Asp Glu Pro Lys Trp Gln Val
            20                  25                  30

Asp Ser Pro Lys Gly Gln Phe Val Asp Ala Thr Ile Ser Val Asp Gln
        35                  40                  45

Gly Thr Trp Met Asn Leu Asp Ile Ser Pro Asp Gly Lys Thr Leu Val
    50                  55                  60

Phe Asp Leu Leu Gly Asp Ile Tyr Thr Met Pro Ile Ser Gly Gly Asn
65                  70                  75                  80

Ala Thr Gln Leu Thr Ser Asp Ile Ala Trp Gln Met Gln Pro Arg Phe
                85                  90                  95

Ser Pro Asn Gly Lys His Ile Ala Phe Thr Ser Asp Gln Gly Gly Gly
            100                 105                 110

Asp Asn Ile Trp Ile Met Asp Leu Asn Gly Glu Asn Gln Ser Ala Val
        115                 120                 125

Thr Asp Glu Thr Phe Arg Leu Leu Asn Ser Pro Ala Trp Ser Pro Asp
    130                 135                 140

Gly Asp Tyr Leu Val Ala Arg Lys His Phe Thr Ala Ser Arg Ser Leu
145                 150                 155                 160

Gly Ala Gly Glu Val Trp Leu Tyr His Lys Ala Gly Gly Lys Gly Val
                165                 170                 175

Gln Leu Thr Lys Arg Ala Asp Asp Gln Lys Asp Leu Gly Glu Pro Met
            180                 185                 190

Phe Ser Pro Asp Gly Arg Tyr Val Tyr Phe Ser His Asp Ala Thr Pro
        195                 200                 205

Gly Lys Thr Phe His Tyr Ser Lys Asp Ser Val Ala Gly Ile Tyr Lys
    210                 215                 220

Ile Lys Arg Tyr Asp Arg Glu Thr Gly Glu Ile Glu Thr Val Ile Ser
225                 230                 235                 240

Gly Met Gly Gly Ala Ile Arg Pro Thr Pro Ser Pro Asp Gly Lys Lys
                245                 250                 255

Leu Ala Tyr Ile Lys Arg Asp Asp Phe Gln Thr Ser Leu Tyr Leu Tyr
            260                 265                 270

Asp Leu Thr Ser Gly Glu His Thr Lys Leu Tyr Asp Lys Leu Glu Arg
        275                 280                 285

Asp Met Gln Glu Thr Trp Ala Ile His Gly Val Tyr Pro Thr Ile Ala
    290                 295                 300

Trp Thr Pro Asp Asn Gln Gln Leu Val Phe Trp Ala Gly Gly Thr Ile
305                 310                 315                 320

His Lys Leu Asp Val Ser Asp Lys Ser Val Glu Thr Ile Ala Phe Lys
                325                 330                 335
```

-continued

```
Val Gln Thr Thr Lys Lys Ile Gln Lys Ala Val Arg Phe Thr Gln Asn
            340                 345                 350

Leu Asp Thr Asp Glu Phe Asp Val Lys Met Leu Arg Asn Val Gln Ile
            355                 360                 365

Ser Pro Asp Gly Glu Thr Ala Ile Phe Glu Ala Leu Gly His Ile Tyr
370                 375                 380

Lys Arg Asp Leu Glu Ser Gly Lys Ile Lys Arg Leu Thr Lys Gln Thr
385                 390                 395                 400

Asp His Tyr Glu Leu Phe Ala Gln Tyr Ser Arg Asp Gly Lys Lys Ile
            405                 410                 415

Val Tyr Thr Thr Trp Asp Asn Glu Gln Gly Gln Val Arg Val Val
            420                 425                 430

Ser Ala Ser Ser Gly Arg Gly Asp Thr Ile Thr Glu Gln Pro Gly Lys
            435                 440                 445

Tyr Val Glu Pro Thr Phe Ser Pro Asp Gly Lys Thr Val Val Tyr Arg
450                 455                 460

Lys Ala Thr Gly Gly Ser Ile Leu Asn Pro Lys Trp Ser Leu Asn Pro
465                 470                 475                 480

Gly Val Tyr Ser Val Ser Thr Lys Gly Gly Lys Ser Glu Leu Ile Ser
            485                 490                 495

Lys Asn Gly Tyr Gln Pro Gln Phe Gly Ala Ala Asn Asp Arg Val Tyr
            500                 505                 510

Ile Met Ser Pro Trp Pro Lys Pro Thr Leu Ser Val Glu Leu Asp
515                 520                 525

Thr Lys Lys Val Arg Lys Leu Tyr Glu Ser Glu His Ala Thr Glu Phe
530                 535                 540

Arg Val Ser Pro Asp Gly Gln Tyr Leu Ala Phe Ala Glu Arg Phe Lys
545                 550                 555                 560

Val Phe Val Thr Pro Phe Val Glu Asn Gly Lys Thr Leu Asn Ile Ser
            565                 570                 575

Pro Thr Asp Asn Gln Phe Pro Ile Glu Gln Leu Ser Val Arg Ala Gly
            580                 585                 590

Glu Asn Ile Ser Trp Ser Ala Asn Ser Asn Lys Leu Tyr Trp Thr Leu
            595                 600                 605

Gly Pro Glu Leu Tyr His Ala Ser Leu Glu Gly Met Phe Ala Ile Asn
610                 615                 620

Lys Ala Asp Asp Lys Asp Phe Lys Val Lys Ser Gly Asp Asn Ile Ser
625                 630                 635                 640

Phe Ser Lys Lys Met Ala Glu Pro Lys Gly Met Ile Ala Leu Thr Gly
            645                 650                 655

Ala Lys Ile Ile Thr Met Asp Gly Glu Lys Val Ile Glu Asn Gly Val
            660                 665                 670

Ile Ile Thr Asp Gly Lys His Ile Lys Ala Ile Gly Thr Ala Ala Glu
            675                 680                 685

Val Ser Ile Pro Lys Gly Ala Lys Val Val Asp Val Thr Gly Lys Thr
690                 695                 700

Ile Met Pro Gly Ile Val Asp Ala His Ala His Gly Ser Gln Ala Ser
705                 710                 715                 720

Asp Glu Ile Ile Pro Gln Gln Asn Trp Lys Asn Phe Ala Gly Leu Ala
            725                 730                 735

Leu Gly Val Thr Thr Ile His Asp Pro Ser Asn Asp Thr Ser Glu Ile
            740                 745                 750

Phe Thr Ala Ser Glu Met Gln Lys Ala Gly Met Ile Val Gly Pro Arg
755                 760                 765
```

Ile Phe Ser Thr Gly Thr Ile Leu Tyr Gly Ala Asn Met Pro Gly Tyr
            770                 775                 780

Thr Ser His Ile Asp Ser Leu Asp Asp Ala Lys Phe His Leu Glu Arg
785                 790                 795                 800

Leu Lys Lys Val Gly Ala Phe Ser Val Lys Ser Tyr Asn Gln Pro Arg
                805                 810                 815

Arg Glu Gln Arg Gln Gln Val Ile Glu Ala Gly Arg Glu Leu Gln Met
            820                 825                 830

Met Val Val Pro Glu Gly Gly Ser Leu Leu Gln His Asn Leu Ser Met
            835                 840                 845

Ile Val Asp Gly His Thr Gly Ile Glu His Ser Ile Pro Val Glu His
850                 855                 860

Ile Tyr Asp Asp Ile Lys Gln Leu Trp Ser Gln Ser Asp Val Gly Tyr
865                 870                 875                 880

Thr Pro Thr Leu Val Val Ala Tyr Gly Gly Ile Trp Gly Glu Asn Tyr
                885                 890                 895

Trp Tyr Asp Lys Thr Asp Val Trp Asn His Pro Arg Leu Ser Lys Phe
            900                 905                 910

Val Pro Lys Asn Gln Leu Leu Pro Arg Ser Met Arg Arg Val Lys Ala
            915                 920                 925

Pro Glu His His Tyr Asn His Phe Asn Asn Ala Arg Val Ala Ala Glu
            930                 935                 940

Leu Gln Asp Leu Gly Val Leu Asn Leu Gly Ala His Gly Gln Arg
945                 950                 955                 960

Glu Gly Leu Gly Ala His Trp Glu Met Trp Met Phe Ala Gln Gly Gly
                965                 970                 975

Met Thr Pro Leu Glu Ala Ile Arg Ala Ser Thr Leu Asp Pro Ala Lys
            980                 985                 990

Tyr Leu Gly Leu Asp Lys Asn Val  Gly Ser Leu Glu Val  Gly Lys Leu
            995                1000                1005

Ala Asp  Leu Met Val Ile Asp  Gly Asp Pro Leu Ser  Asn Ile Arg
    1010                1015                1020

Asp Ser  Asp Lys Ile Asp Tyr  Thr Met Ile Asn Gly  Arg Leu Phe
    1025                1030                1035

Asn Ala  Ala Thr Met Val Glu  Val Gly Lys Gln  Arg Lys Pro
    1040                1045                1050

Leu Tyr  Phe Glu Asn Asn Lys
    1055                1060

<210> SEQ ID NO 6
<211> LENGTH: 23
<212> TYPE: PRT
<213> ORGANISM: Pseudoalteromonas tunicata
<220> FEATURE:
<221> NAME/KEY: misc_feature
<223> OTHER INFORMATION: Peptide signal de la proteine putative non
      caracterisee A4CBN2

<400> SEQUENCE: 6

Met Lys Lys Phe Ile Tyr Ser Ser Val Ala Phe Ala Val Ala Met Thr
1               5                   10                  15

Phe Ser Pro Ala Ser Phe Ala
            20

<210> SEQ ID NO 7
<211> LENGTH: 27
<212> TYPE: PRT

```
<213> ORGANISM: Shewanella denitrificans
<220> FEATURE:
<221> NAME/KEY: misc_feature
<223> OTHER INFORMATION: Peptide signal de l'Amidohydrolase (precurseur)
      Q12TB8

<400> SEQUENCE: 7

Met Leu Met Leu Ser Ile Lys Phe Thr Pro Leu Tyr Thr Ala Ile Ala
1               5                   10                  15

Leu Thr Leu Gly Cys Ser Ser Leu Val Tyr Ala
            20                  25

<210> SEQ ID NO 8
<211> LENGTH: 22
<212> TYPE: PRT
<213> ORGANISM: Alteromonodales bacterium TW-7
<220> FEATURE:
<221> NAME/KEY: misc_feature
<223> OTHER INFORMATION: Peptide signal de la proteine putative non
      caracterisee A0Y053

<400> SEQUENCE: 8

Met Lys Lys Leu Leu His Thr Ala Leu Ala Leu Ser Val Ser Leu Ala
1               5                   10                  15

Leu Gly Gln Ala His Ala
            20

<210> SEQ ID NO 9
<211> LENGTH: 22
<212> TYPE: PRT
<213> ORGANISM: Pseudoalteromonas haloplanktis
<220> FEATURE:
<221> NAME/KEY: misc_feature
<223> OTHER INFORMATION: Peptide signal de la proteine putative non
      caracterisee Q3IKL4

<400> SEQUENCE: 9

Met Lys Lys Met Leu Gln Thr Val Leu Ala Leu Ser Val Ser Leu Ala
1               5                   10                  15

Leu Gly Asn Ala Gln Ala
            20
```

4S-IOTA-CARRAGEENAN SULFATASE AND USE THEREOF TO OBTAIN ALPHA-CARRAGEENAN

The present invention relates to 4S-iota-carrageenan sulfatase and to the use thereof for partially or totally converting iota-carrageenan into iota-/alpha-carrageenan or into alpha-carrageenan. It also relates to the method for extracting said enzyme from a *Pseudoalteromonas* bacteria population or from red marine algae. Finally, the present invention relates to the use of 4S-iota-carrageenan sulfatase to prepare a texturizing agent containing alpha-carrageenan.

Carrageenans define families of sulfated galactans isolated from the extra-cellular matrix of red marine algae. These anionic polysaccharides have unique rheological properties and are used as texturizing agents in the food-processing, parapharmacy and cosmetics industries. Carrageenans are composed of a sequence of D-galactoses bonded alternatively by alpha (1-3) and beta (1-4) bonds. These polysaccharides are distinguished by the presence or not of a 3,6 anhydrous bridge on the alpha bonded (1-3) galactose residue and by their level of sulfation.

Carrageenans possess a wide diversity of chemical structures that are correlated with a large spectrum of their functional properties. Consequently, each source of algae corresponds to properties and applications that are specific to it. Moreover, depending on the structure of the carrageenan (for example alpha- or iota-carrageenan) and the origin of the algae (cultivated or collected in the natural environment), the abundance and the cost of these macromolecules are highly variable. The tonnage of carrageenans exploited is limited by the quantity of red algae available. In the case of alpha-carrageenan, this polysaccharide has been observed in the algae *Catenella nipae*. In nature, alpha-carrageenan is always associated with iota-carrageenan. The article of Zablackis and Santos (1986) may be cited, which describes for the first time the presence of alpha-carrageenan and the work of Falshaw et al. (1996), who carried out the structural analysis of the polysaccharide.

In this context, the use of enzymes to manipulate the chemical structure of carrageenans makes it possible to control the supply and the functional properties of carrageenans.

In the present invention, the Inventors have identified from extracts of bacteria a sulfatase that acts on iota-carrageenan, the 4S-iota-carrageenan sulfatase. This enzyme makes it possible to catalyze the specific desulfation in position 4 of iota-carrageenan, leading in a single step to alpha-carrageenan or to a hybrid structure of alpha-/iota-carrageenan type. The reaction takes place without apparent modification of the molecular weight of the carrageenan, thereby enabling a notable improvement in the gelifying properties. 4S-iota-carrageenan sulfatase has been purified and sequenced.

The Inventors have thus been able to determine that the hypothetical protein Q3IKL4 (SEQ ID NO: 5) of the marine bacterium *Pseudoalteromonas haloplanktis*, the genome of which has been entirely sequenced, and which is referenced in the TrEMBL protein data bank accessible on the Internet, corresponds in fact to 4S-iota-carrageenan sulfatase.

The present invention offers numerous advantages for the following reasons:

The invention offers the possibility of not being reliant on certain resources of algae, the costs of which become very high.

The invention makes it possible to produce carrageenans of hybrid structures from carrageenans extracted from cultivated algae (inexpensive).

The invention also makes it possible to produce alpha-carrageenan, which is a not very abundant structure, or even inexistent in nature.

Thanks to the sequencing of 4S-iota-carrageenan sulfatase, it is now possible to produce and exploit this enzyme on a large scale.

Thus, according to a first aspect, the present invention relates to an isolated polypeptide comprising an amino acid sequence having at least 65% of identity with the sequence SEQ ID No 2 or the sequence SEQ ID No 4.

The present invention also relates to an isolated polypeptide consisting of an amino acid sequence having at least 65% of identity with the sequence SEQ ID No 2 or the sequence SEQ ID No 4.

In the present invention, by an isolated polypeptide comprising or consisting of an amino acid sequence having at least 65% of identity, preferably at least 70%, 75%, 80%, 85%, 90%, 93%, 94%, 95%, 96%, 97%, 98%, 99% of identity with the sequence SEQ ID No 2 or the sequence SEQ ID No 4, it is meant a polypeptide that has the 4S-iota-carrageenan sulfatase function. The 4S-iota-carrageenan sulfatase is an enzyme that makes it possible to convert iota-carrageenan into alpha-carrageenan by specific desulfation (elimination of a $SO_3$ group) in position 4 of the iota-carrageenan (see diagram below). The molecular weight of the 4S-iota-carrageenan sulfatase is around 110 kDaltons.

Diagram 1: Enzymatic reaction catalyzed by the 4S-iota-carrageenan sulfatase

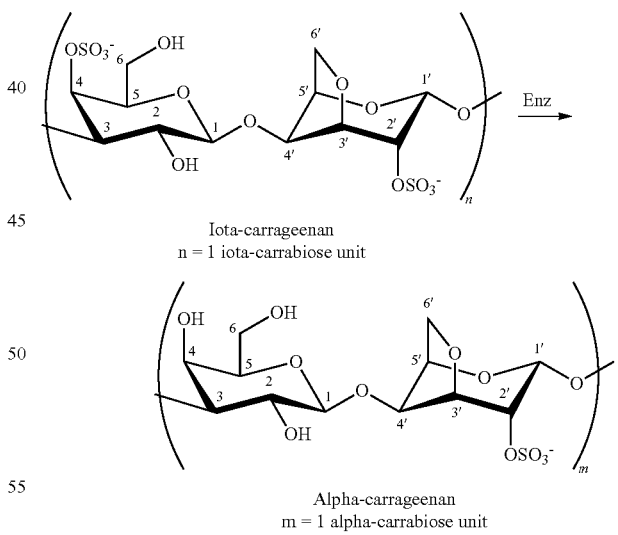

Iota-carrageenan
n = 1 iota-carrabiose unit

Alpha-carrageenan
m = 1 alpha-carrabiose unit

The iota-carrageenan corresponds to at least one iota-carrabiose unit, preferably a sequence of iota-carrabiose units. These are then referred to as oligomers or polymers of iota-carrageenan, depending on the number n of repetition units of the iota-carrabiose unit.

The iota-carrabiose unit(s) may be associated with at least one other repetition unit, thereby forming a hybrid iota-carrageenan, or even a hybrid oligo-iota-carrageenan or a copolymer of iota-carrageenan when several iota-carrabiose units are associated with other repetition units within a same chain of polysaccharides.

In the present invention, the terms polypeptide, polypeptide sequence, peptide, peptide sequence, protein, protein sequence, amino acid sequence are interchangeable.

It should be understood here that the invention does not relate to the 4S-iota-carrageenan sulfatase in natural form, in other words taken in its natural environment, but the 4S-iota-carrageenan sulfatase isolated and/or purified from natural sources, or instead obtained by genetic recombination or chemical synthesis.

By "percentage of identity" between two sequences of nucleic acid or amino acid according to the present invention, it is meant a percentage of identical nucleotides or amino acids between the two sequences to be compared, obtained after the best alignment (optimal alignment), this percentage being purely statistical and the differences between the two sequences being distributed randomly and over their whole length. Comparisons of sequences between two sequences of nucleic acid or amino acid are conventionally carried out by comparing said sequences after having aligned them in an optimal manner, said comparison being able to be carried out by segment or by "comparison window". The optimal alignment of sequences for the comparison may be carried out, apart from manually, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444], by means of computer software using these algorithms (GAP, BESTFIT, FASTA and TFASTA in the Wisconsin Genetics Software Package, Genetics Computer Group, 575 Science Dr., Madison, Wis., or instead by BLAST N or BLAST P comparison software).

The percentage of identity between two sequences of nucleic acid or amino acid is determined by comparing said two sequences aligned in an optimal manner in which the nucleic acid or amino acid sequence to compare may comprise additions or deletions by comparison to the reference sequence for an optimal alignment between said two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 to obtain the percentage of identity between said two sequences.

For example, the BLAST program, "BLAST2 sequences" could be used (Tatusova et al., "Blast 2 sequences—a new tool for comparing protein and nucleotide sequences", FEMS Microbiol., 1999 Lett. 174:247-250) available from the Basic Local Alignment Search Tool of the National Center for Biotechnology Information (NCBI) website (link "Specialized BLAST", "Align two sequences using BLAST (bl2seq)"), the percentage of identity between the two sequences to be compared being calculated directly by the program.

By amino acid sequence exhibiting or having at least 65% of identity, preferably at least 70%, 75%, 80%, 85%, 90%, 93%, 94%, 95%, 96%, 97%, 98%, 99% of identity with an amino acid sequence of reference, those exhibiting, by comparison to the reference sequence, certain modifications in particular a deletion, addition or substitution of at least one amino acid, a truncation or a lengthening are preferred. In the case of a substitution of one or more consecutive or non consecutive amino acid(s), substitutions are preferred in which the substituted amino acids are replaced by "equivalent" amino acids. The expression "equivalent amino acids" here aims to designate any amino acid capable of being substituted by one of the amino acids of the basic structure without however essentially modifying the 4S-iota-carrageenan sulfatase function.

These amino acids may be determined either by relying on their homology of structure with the amino acids that they replace, or on the results of comparative tests of the 4S-iota-carrageenan sulfatase function between the different sequences likely to be carried out.

As a non limiting example, table 1 below summarises the possibilities of substitution capable of being carried out without an in depth modification of the resulting 4S-iota-carrageenan sulfatase function, the reverse substitutions being naturally conceivable under the same conditions.

TABLE 1

| Original residue | Substitution(s) |
|---|---|
| Ala (A) | Val, Gly, Pro |
| Arg (R) | Lys, His |
| Asn (N) | Gin |
| Asp (D) | Glu |
| Cys (C) | Ser |
| Gin (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (Y) | Leu, Ala |

The isolated polypeptide according to the present invention may comprise, in addition to the amino acid sequence having at least 65% of identity with the sequence SEQ ID NO: 2 or the sequence SEQ ID NO: 4, at least one other peptide sequence such as a signal peptide or a CBM (for "carbohydrate-binding module"). Such modules are well known to those skilled in the art and are notably accessible on the Internet on the Carbohydrate-Active enZYmes (CAZy) online database. It can also be a protein such as an enzyme, for example a carrageenase, in which case it is referred to as a fusion polypeptide. Other possibilities may be envisaged and the list of other peptide sequences included in the polypeptide according to the invention is not limitative. When the isolated polypeptide according to the present invention also comprises a signal peptide, said signal peptide has the function of exporting the protein of amino acid sequence having at least 65% of identity with the sequence SEQ ID NO: 2 or the sequence SEQ ID NO: 4, to a particular cell compartment, or even to the exterior of a cell. In the present invention, signal peptides of carrageenases, advantageously the signal peptides of the carrageenases of *Pseudoalteromonas haloplanktis, Pseudoalteromonas carrageenovora, Pseudoalteromonas tunicata, Alteromonadales bacterium*, or *Shewanella denitrificans* will be preferred. In an even more preferred manner, the signal peptide is selected from the group constituted of peptides of sequence SEQ ID NO: 6, SEQ ID NO: 7, SEQ ID NO: 8, and SEQ ID NO: 9.

TABLE 2

| Organism | Sequence of the signal the peptide | Sequence number |
|---|---|---|
| *Pseudoalteromonas tunicata* | MKKFIYSSVAFAVAMTFSPASFA | SEQ ID N° 6 |
| *Shewanella denitrificans* | MLMLSIKFTPLYTAIALTLGCSSLVY A | SEQ ID N° 7 |
| *Alteromonodales bacterium TW-7* | MKKLLHTALALSVSLALGQAHA | SEQ ID N° 8 |
| *Pseudoalteromonas haloplanktis* | MKKMLQTVLALSVSLALGNAQA | SEQ ID N° 9 |

Preferably, the isolated polypeptide according to the present invention comprising or consisting of the amino acid sequence having at least 65% of identity with SEQ ID No 2 or SEQ ID No 4, has a size comprised between 1025 and 1070 amino acids, advantageously between 1027 and 1060 amino acids, even more advantageously between 1028 and 1055 amino acids, even more advantageously between 1030 and 1045 amino acids, even more advantageously between 1035 and 1040 amino acids, in a manner preferred to all others 1038 amino acids.

According to another preference, the sequence of the isolated polypeptide according to the present invention comprising or consisting of the amino acid sequence having at least 65% of identity with SEQ ID No 2 or SEQ ID No 4 corresponds to that of a 4S-iota-carrageenan sulfatase of *Pseudoalteromonas*.

Also in a preferred manner, the sequence of the isolated polypeptide according to the present invention comprising or consisting of the amino acid sequence having at least 65% of identity with SEQ ID No 2 or SEQ ID No 4, corresponds to that of a 4S-iota-carrageenan sulfatase of *Pseudoalteromonas* and has a size comprised between 1025 and 1055 amino acids, advantageously between 1030 and 1045 amino acids, between 1035 and 1040 amino acids, in a manner preferred to all others 1038 amino acids.

In an even more preferred manner, the present invention relates to an isolated polypeptide comprising an amino acid sequence having at least 95% of identity with an amino acid sequence selected from the group constituted of the sequences SEQ ID No 2 and SEQ ID No 4.

Also in a preferred manner, the present invention relates to an isolated polypeptide consisting of an amino acid sequence having at least 95% of identity with an amino acid sequence selected from the group constituted of the sequences SEQ ID No 2 and SEQ ID No 4.

In a manner preferred to all others, the present invention also relates to an isolated polypeptide comprising an amino acid sequence selected from the group constituted of the sequences SEQ ID No 2 and SEQ ID No 4.

Also in a manner preferred to all others, the present invention relates to an isolated polypeptide consisting of an amino acid sequence selected from the group constituted of the sequences SEQ ID No 2 and SEQ ID No 4.

According to another aspect, the present invention relates to an isolated polynucleotide selected from the following polynucleotides:
a) a polynucleotide, DNA or RNA, coding the polypeptide according to the present invention as defined above; and
b) a complementary polynucleotide of a polynucleotide as defined in a).

By polynucleotide, polynucleotide sequence, nucleic acid, nucleic sequence or nucleic acid, terms which are indiscriminately designated in the present description, it is meant a precise sequence of nucleotides, modified or not, making it possible to define a fragment or a region of a nucleic acid, comprising or not non natural nucleotides, and which can correspond equally well to a double strand DNA, a single strand DNA, or transcription products of said DNA.

It must also be understood here that the present invention does not relate to nucleotide sequences in their natural chromosome environment, in other words in the natural state. They are sequences that have been isolated and/or purified, in other words that they have been withdrawn directly or indirectly, for example by copying, their environment having been at least partially modified. Isolated nucleic acids obtained by genetic recombination or by chemical synthesis are also intended to be designated herein.

Preferably, the polynucleotide that codes the polypeptide according to the present invention comprises a nucleotide sequence having at least 65% of identity, preferably at least 70%, 75%, 80%, 85 t, 90%, 93%, 94%, 95%, 96%, 97%, 98%, 99% of identity with the sequence SEQ ID No 1 or the sequence SEQ ID No 3.

According to another preference, the polynucleotide that codes the polypeptide according to the present invention consists of a nucleotide sequence having at least 65% of identity, preferably at least 70%, 75%, 80%, 85%, 90%, 93%, 94%, 95%, 96%, 97 t, 98%, 99% of identity with the sequence SEQ ID No 1 or the sequence SEQ ID No 3.

By olynucleotide having at least 65% of identity, preferably at least 70%, 75%, 80%, 85%, 90%, 93%, 94%, 95%, 96%, 97%, 98%, 99% of identity with a sequence, it is meant polynucleotides exhibiting, by comparison to the reference polynucleotide, certain modifications such as in particular a deletion, a truncation, a lengthening, a chimeric fusion and/or a substitution, notably isolated. It preferably involves sequences coding the same amino acid sequences as the reference sequence, this linked to the degenerescence of the genetic code, or complementary sequences which are capable of hybridizing specifically with the nucleotide sequences of reference, preferably under high-stringency conditions.

A hybridization under high-stringency conditions means that the conditions of temperature and of ionic force are selected in such a way that they make it possible to maintain the hybridization between two complementary DNA fragments.

In a more preferred manner, the nucleotide sequence is selected from the group constituted of the sequence SEQ ID No 1 and the sequence SEQ ID No 3.

The present invention also relates to an expression vector comprising a polynucleotide according to the present invention as defined above.

The invention particularly relates to cloning and/or expression vectors which contain a nucleotide sequence according to the invention.

The vectors according to the invention preferably comprise elements that enable the expression and/or the secretion of nucleotide sequences in a determined host cell. The vector must then comprise a promoter, signals for initiation and termination of the translation, as well as suitable regions for regulating the transcription. It must be able to be maintained in a stable manner in the host cell and may optionally possess particular signals that specify the secretion of the translated protein. These different elements are selected and optimized by one skilled in the art depending on the host cell used. To this end, the nucleotide sequences according to the invention may be inserted into autonomous replication vectors within the selected host, or be integrative vectors of the selected host.

Such vectors are prepared by methods commonly used by those skilled in the art, and the resulting clones may be introduced into a suitable host by standard methods, such as lipofection, electroporation, thermal shock, or chemical methods.

The vectors according to the invention are for example vectors of plasmidic or viral origin. They are useful for transforming host cells in order to clone or express the nucleotide sequences according to the invention.

The invention also comprises a host cell comprising a vector according to the present invention or transformed by a vector according to the present invention.

The host cell may be selected from prokaryotic or eukaryotic systems, for example bacterial cells such as *E. coli* or *Bacillus*, but also yeast cells or animal cells.

The invention also relates to organisms that contain a cell transformed according to the invention, such as red algae, micro-algae or terrestrial plants.

According to another aspect, the invention relates to a method for producing a polypeptide according to the present invention comprising the following steps:

a) culturing in a suitable medium and culture conditions a population of host cells according to the invention; and b) recovering said polypeptides thereby produced from the culture medium or the population of cultivated host cells.

The cells transformed according to the invention may be used in methods for preparing recombinant polypeptides according to the invention. The methods for preparing a polypeptide according to the invention in recombinant form, characterized in that they implement a vector and/or a cell transformed by a vector according to the invention, are themselves included in the present invention. Preferably, a cell transformed by a vector according to the invention is cultivated under conditions that enable the expression of said polypeptide and said recombinant polypeptide is recovered.

As has been said, the cell host may be selected from prokaryotic or eukaryotic systems. In particular, it is possible to identify nucleotide sequences according to the invention, facilitating the secretion in such a prokaryotic or eukaryotic system. A vector according to the invention bearing such a sequence may thus be used for the production of recombinant proteins, intended to be secreted. Indeed, the purification of said recombinant proteins of interest will be facilitated by the fact that they are present in the supernatant of the cell culture rather than inside the host cells. Alternatively, in the case of prokaryotic systems, the proteins may be overexpressed in the periplasmic space of the bacteria, which makes it possible to handle occasional important volumes of culture media.

The polypeptides according to the invention may also be prepared by chemical synthesis. Such a preparation method is also a subject matter of the invention. One skilled in the art knows the chemical synthesis methods, for example techniques implementing solid phases (see in particular Steward et al., 1984, "Solid phase peptide synthesis", Pierce Chem. Company, Rockford, 111, 2eme ed.) or techniques using partial solid phases, by condensation of fragments or by a conventional synthesis in solution. The polypeptides obtained by chemical synthesis and which may comprise corresponding non natural amino acids are also included in the invention.

The polypeptides obtainable by a production method according to the present invention are also included in the invention.

According to another aspect, the invention relates to a method for obtaining a 4S-iota-carrageenan sulfatase from a bacteria population capable of containing the 4S-iota-carrageenan sulfatase comprising:

(a) culturing the bacteria population in a medium and culture conditions suitable to obtain the 4S-iota-carrageenan sulfatase in the culture medium, and (b) obtaining the 4S-iota-carrageenan sulfatase from the culture medium obtained at step (a).

In the present invention, it is meant by bacteria population capable of containing the 4S-iota-carrageenan sulfatase, a bacteria population in which it is assumed that it expresses the 4S-iota-carrageenan sulfatase. It is preferably a bacteria population having a carrageenase activity, in other words an activity making it possible to degrade a carrageenan ("carrageenolytic bacteria population"). Such bacteria are notably described in the scientific article Michel et al., 2006. The bacteria population having a carrageenase activity is preferably a bacteria population belonging to the class Gammaproteobacteria, Flavobacteria or Sphingobacteria. Preferably, it is a bacteria population belonging to the genus *Alteromonas, Pseudoalteromonas, Cobetia* or *Zobellia*. In an even more preferred manner, the bacteria population belongs to the genus *Pseudoalteromonas*.

Preferably, said bacteria population contains 4S-iota-carrageenan sulfatase.

Preferably, the invention relates to the method for obtaining 4S-iota-carrageenan sulfatase from the *Pseudoalteromonas haloplanktis* and/or *Pseudoalteromonas carrageenovora* bacteria population.

A suitable culture medium for a bacteria population according to the invention is the ZoBell medium (see the composition in the Examples section below). It may also be the DIFCO 2216 culture medium ("bacto marine broth"), the composition of which is generally as follows: Bacto peptone 5.00 g, yeast extract 1.00 g, Fe(III) citrate 0.10 g, NaCl 19.45 g, $MgCl_2$ (anhydrous) 5.90 g, $Na_2SO_4$ 3.24 g, $CaCl_2$ 1.80 g, KCl 0.55 g, $Na_2CO_3$ 0.16 g, KBr 0.08 g, $SrCl_2$ 34.00 mg, $H_3BO_3$ 22.00 mg, Na-silicate 4.00 mg, NaF 2.40 mg, $(NH_4)NO_3$ 1.60 mg, $Na_2HPO_4$ 8.00 mg.

Advantageously, 37.4 g of this mixture are added to 1 L of osmosized water to obtain 1 L of liquid medium (the site http://www.bd.com/ds/technicalCenter/inserts/difcoBbl-Manual.asp describes the medium preparation procedure). It may also be a marine gelose, which contains synthetic sea water ingredients (NaCl, $MgCl_2$, $Na_2SO_4$, $CaCl_2$, KCl, etc.) as well as peptone and yeast extract as source of organic nitrogen, vitamins and minerals. Suitable conditions for culturing the bacteria population according to the invention include the temperature, advantageously between 15 and 20° C., the culture time, advantageously from 24 to 36 hours, and under agitation, advantageously between 200 and 250 rpm.

Preferably, the culture medium of step (a) further contains a carrageenan, in order to induce a 4S-iota-carrageenan sulfatase activity. In an even more preferred manner, the carrageenan is selected from iota-carrageenan, lambda-carrageenan and nu-carrageenan.

In a manner preferred to all others, when the bacteria population is a *Pseudoalteromonas carrageenovora* bacteria population, the culture medium of step (a) further contains lambda-carrageenan, in order to induce a 4S-iota-carrageenan sulfatase activity.

According to another alternative, when the bacteria population is a *Pseudoalteromonas haloplanktis* bacteria population, the culture medium from step (a) further contains iota-carrageenan or an iota/nu-carrageenan mixture, in order to induce a 4S-iota-carrageenan sulfatase activity. Advantageously, the concentration of carrageenan added to the culture medium at step (a) is comprised between 0.5 and 1.5 g/L, preferably 1.0 g/L. In an even more advantageous manner, the concentration of lambda-carrageenan added to the culture medium at step (a) is comprised between 0.5 and 1.5 g/L, preferably 1.0 g/L.

Preferably, the production method according to the invention is such that step (b) includes the following sub-steps:

(b1) centrifuging the culture medium obtained at step (a), and (b2) obtaining 4S-iota-carrageenan sulfatase from the supernatant and/or from the culture pellet obtained at step (b1), advantageously from the culture pellet.

To obtain the 4S-iota-carrageenan sulfatase from the supernatant, said supernatant is preferably concentrated, for example by precipitation to saturation in ammonium sulfate.

To obtain the 4S-iota-carrageenan sulfatase from the pellet, said pellet is preferably re-suspended in a suitable buffer such as Tris HCl buffer, and the cells are then lysed by any suitable technique, for example by using a French press. A centrifugation is carried out lastly to eliminate cell debris.

In a manner preferred to all others, the method for obtaining a 4S-iota-carrageenan sulfatase from a *Pseudoalteromonas carrageenovora* bacteria population comprises:

(a) culturing the *Pseudoalteromonas carrageenovora* bacteria population in a medium and culture conditions suitable to obtain 4S-iota-carrageenan sulfatase in the culture medium, said medium further containing lambda-carrageenan, (b1) centrifuging the culture medium obtained at step (a), and (b2) obtaining 4S-iota-carrageenan sulfatase from the culture pellet obtained at step (b1).

According to another alternative preferred to all others, the method for obtaining a 4S-iota-carrageenan sulfatase from a *Pseudoalteromonas haloplanktis* bacteria population comprises:

(a) culturing the *Pseudoalteromonas haloplanktis* bacteria population in a medium and culture conditions suitable to obtain 4S-iota-carrageenan sulfatase in the culture medium, said medium moreover containing iota-carrageenan or a iota/nu-carrageenan mixture, (b1) centrifuging the culture medium obtained at step (a), and (b2) obtaining 4S-iota-carrageenan sulfatase from the culture pellet obtained at step (b1).

Step (b) of obtaining 4S-iota-carrageenan sulfatase from the culture medium may be carried out according to different purification techniques well known to one skilled in the art. The same is true for step (b2) of obtaining 4S-iota-carrageenan sulfatase from the supernatant and/or the culture pellet. It involves in general purifying the protein, in this instance the 4S-iota-carrageenan sulfatase. The most commonly employed purification techniques make use of chromatographic methods, such as hydrophobic interaction chromatography (for example on phenyl sepharose column), and/or chromatography on ion exchange column. Preferably, the chromatographic methods are implemented successively. In an even more preferred manner, firstly hydrophobic interaction chromatography is used then ion exchange column chromatography. Often, between these successive purification steps, it is advisable to eliminate the salts or products used in the chromatographies. To do this, a dialysis and/or an ultrafiltration is used.

Preferably, after the hydrophobic interaction chromatography, the different fractions collected are dialysed then tested for their ability to desulfate iota-carrageenan (sulfatase activity assay). The fractions capable of desulfating iota-carrageenan are collected together and dialysed, then the sample obtained is purified on an ion exchange column. Then the different fractions collected are tested for their ability to desulfate iota-carrageenan (sulfatase activity assay). It is also possible to analyze the degree of purity of the different fractions by electrophoresis on polyacrylamide gel, the band corresponding to the 4S-iota-carrageenan sulfatase then being around 110 kDaltons.

Preferably, the method for obtaining 4S-iota-carrageenan sulfatase according to the present invention comprises, after step (b) (or step b2), the following additional step:

(c) dosage of the 4S-iota-carrageenan sulfatase activity.

The dosage of the 4S-iota-carrageenan sulfatase activity is carried out by dosing the released sulfate. To do this, the sample to be dosed (different fractions separated or collected together) is incubated with the carrageenan, advantageously iota-carrageenan, preferably at a concentration of 1.2%, preferably volume to volume. After a minimum necessary incubation time, advantageously at least 15 hours, and at a temperature comprised between 25 and 37° C., the reaction mixture is preferably diluted, then is centrifuged (Microcons 10, Amicon). Then the quantity of sulfate present in the filtrate is advantageously assayed by high performance ion exchange chromatography. Lastly, the detection of the anions may be carried out by conductimetry. To do this, a detector of the ED40 type (Dionex) equipped with an ASRSD ultra-II-4 mm suppressor is preferably used.

According to another aspect, the present invention relates to a method for extracting a 4S-iota-carrageenan sulfatase from a population of red marine algae, comprising:

(i) isolating a bacteria population capable of containing the 4S-iota-carrageenan sulfatase from the population of red marine algae; and (ii) obtaining 4S-iota-carrageenan sulfatase from the bacteria population obtained at step (i), according to the method as defined above.

The isolation of a bacteria population, such as a bacteria population capable of containing the 4S-iota-carrageenan sulfatase, from a population of marine algae is well known to one skilled in the art and is in particular described in Potin et al, 1991.

According to yet another aspect, the present invention relates to a method for converting a composition containing iota-carrageenan and/or hybrid iota-carrageenan into a composition that contains alpha-carrageenan and/or hybrid alpha-carrageenan, comprising the following steps:

(a) bringing together the composition containing iota-carrageenan and/or hybrid iota-carrageenan, with a solution containing an isolated polypeptide comprising an amino acid sequence having at least 65% of identity with the sequence SEQ ID No 2 or the sequence SEQ ID No 4, under appropriate conditions for the conversion of the composition, and (b) optionally, recovering the composition containing alpha-carrageenan and/or hybrid alpha-carrageenan obtained at step (a).

The isolated polypeptide comprising an amino acid sequence having at least 65% of identity with the sequence SEQ ID No 2 or the sequence SEQ ID No 4 as well as its preferred embodiments are as defined above.

In the present invention, by "composition containing iota-carrageenan and/or hybrid iota-carrageenan", it is meant a solution, a partially gelified solution or a gel containing said iota-carrageenan and/or hybrid iota-carrageenan. In fact, it should be noted that, under experimental conditions such as those of the invention, pure iota-carrageenan gelifies under its own load. Thus, under the experimental conditions, it is not possible to speak stricto sensu of a solution. In addition, under very diluted conditions, the iota-carrageenan does not gelify. Nevertheless, solutions may be obtained with iota-carrageenan for higher temperatures, in other words in general above 40° C. Moreover, the gelification properties are modulated by the structure of the hybrid carrageenans. Thus, for example, since iota-nu-carrageenan is not very gelifying, it is possible to have it more easily in solution form. The same is true for oligo-iota-carrageenans.

In the present invention, by "iota-carrageenan", it is meant a compound constituted of at least one iota-carrabiose unit (n=1) (cf. diagram 1 above). Preferably, it will be an oligo-iota-carrageenan ($1<n\leq20$), or even a polymer of iota-carrageenan ($n\geq20$).

Also, by "hybrid iota-carrageenan", it is meant a compound constituted of at least one iota-carrabiose unit (n=1) and at least one carrabiose unit other than iota-carrabiose (m=1), such as, without nevertheless being limiting thereof, a nu-carrabiose, kappa-carrabiose, mu-carrabiose or alpha-carrabiose unit. Preferably, it will be a hybrid oligo-iota-carrageenan ($1<n+m\leq20$), or even a hybrid polymer of iota-carrageenan ($n+m\geq20$) (copolymer).

Also in the present invention, by "composition containing alpha-carrageenan and/or hybrid alpha-carrageenan", it is meant a composition that contains an iota-carrageenan or a hybrid iota-carrageenan in which at least one iota-carrabiose unit is converted into an alpha-carrabiose unit. The conversion, at least partial, or total, of the composition containing iota-carrageenan and/or hybrid iota-carrageenan into a composition containing alpha-carrageenan and/or hybrid alpha-carrageenan, depends on the experimental conditions, in other words the concentration of enzyme, substrate, temperature, and the time of bringing it together with the enzyme. Preferably, all of the iota-carrabiose units present in the iota-carrageenan and/or the hybrid iota-carrageenan are converted into alpha-carrabiose units.

Step (b) is optional. Indeed, for an experimental analysis, it is not necessary to separate the solution containing the 4S-iota-carrageenan sulfatase from the composition obtained containing alpha-carrageenan and/or hybrid alpha-carrageenan. On the other hand, this separation would be necessary in other applications such as in the biomedical field, in which ultra-filtration could for example be used.

Advantageously, at step (a), the solution containing the polypeptide is added to the reaction medium in order to increase the conversion rate.

Suitable conditions for the conversion of the composition containing iota-carrageenan and/or hybrid iota-carrageenan (substrate) into a composition containing alpha-carrageenan and/or hybrid alpha-carrageenan include the temperature, advantageously between 25 and 37° C., the time of bringing together the composition containing the substrate with the solution containing the enzyme, advantageously from 12 to 25 hours, and the concentration of enzyme and substrate. Preferably, the enzyme and the substrate are mixed volume to volume.

The present invention also relates to a method for converting a composition containing iota-carrageenan and/or hybrid iota-carrageenan present in a population of red algae, into a composition that contains alpha-carrageenan and/or hybrid alpha-carrageenan, comprising the following steps:

(a) bringing together the population of red algae with a solution containing an isolated polypeptide comprising an amino acid sequence having at least 65% of identity with the sequence SEQ ID No 2 or the sequence SEQ ID No 4, under suitable conditions for the conversion of the composition containing the iota-carrageenan and/or the hybrid iota-carrageenan present in a population of red algae, and (b) optionally, recovering the composition containing the alpha-carrageenan and/or hybrid alpha-carrageenan obtained at step (a).

Preferably, the composition containing iota-carrageenan and/or hybrid iota-carrageenan is brought together with a solution containing an isolated polypeptide comprising or consisting of the amino acid sequence selected from the group constituted of the sequence SEQ ID No 2 and the sequence SEQ ID No 4. The composition containing the iota-carrageenan and/or the hybrid iota-carrageenan may be obtained from red marine algae, or instead commercially, especially from CP Kelco, Cargill, or from Sigma.

The invention also relates to the use of an isolated polypeptide comprising an amino acid sequence having at least 65% of identity with the sequence SEQ ID No 2 or the sequence SEQ ID No 4, for the preparation of a texturizing agent comprising alpha-carrageenan and/or hybrid alpha-carrageenan. The texturizing agent may be used in the food processing, parapharmacy and cosmetics industries.

The invention also relates to the use of an isolated polypeptide comprising an amino acid sequence having at least 65% of identity with the sequence SEQ ID No 2 or the sequence SEQ ID No 4, for the preparation of a gelifying agent comprising alpha-carrageenan and/or hybrid alpha-carrageenan.

The invention also relates to the use of an isolated polypeptide comprising an amino acid sequence having at least 65% of identity with the sequence SEQ ID No 2 or the sequence SEQ ID No 4, for the preparation of a thickening agent comprising alpha-carrageenan and/or hybrid alpha-carrageenan.

According to another aspect, the present invention relates to the use of an isolated polypeptide comprising an amino acid sequence having at least 65% of identity with the sequence SEQ ID No 2 or the sequence SEQ ID No 4, for partially or totally converting a composition containing iota-carrageenan and/or hybrid iota-carrageenan, into a composition that contains alpha-carrageenan and/or hybrid alpha-carrageenan.

Preferably, the amino acid sequence is selected from the group constituted of the sequence SEQ ID No 2 and the sequence SEQ ID No 4.

Also in a preferred manner, the composition containing iota-carrageenan and/or hybrid iota-carrageenan is obtained from red marine algae.

The present invention relates to an isolated polypeptide comprising or consisting of an amino acid sequence having at least 65%, of identity with the sequence SEQ ID 10 No 2 or the sequence SEQ ID No 4, excluding the polypeptide of sequence SEQ ID No 5.

The examples and figures that follow make it possible to illustrate the present invention without however limiting its scope.

FIGURE CAPTIONS

FIG. 1: SDS-PAGE (12%). The size marker (M) is a commercial mixture (BioRad Precision) of 9 proteins characterized by molecular weights between 250 and 10 kD.

FIG. 2: Primary structure of the hypothetical protein Q3IKL4 (SEQ ID NO: 5) of *Pseudoalteromonas haloplanktis*. In bold boxed solid line or bold underlined the peptides deduced from LC/MS-MS experiments (bold and boxed solid line) or de novo (bold and underlined). In bold and boxed broken line, the peptides predicted by the MALDI experiments.

Figure 3:
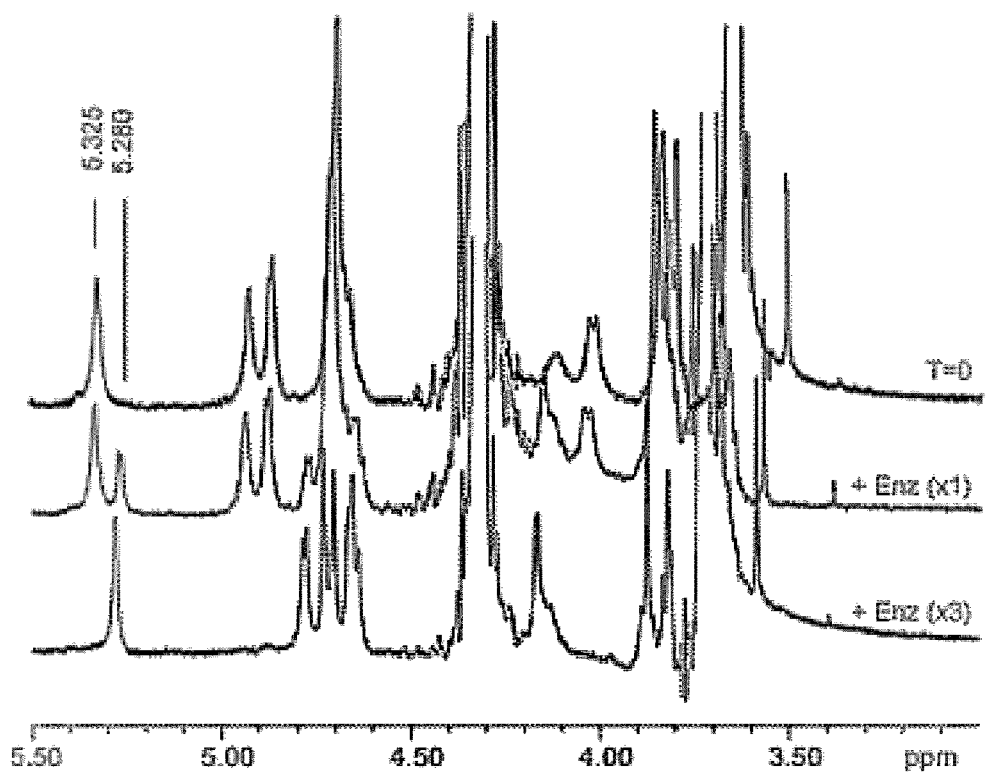

FIG. 3: Proton NMR spectra recorded on iota-carrageenan incubated with purified 4S-iota-caragenan sulfatase which leads to the formation of alpha-carrageenan. Curve "T=0": iota-carrageenan before addition of the enzyme; curve "+Enz (*1)": after 15 hours of incubation at 35° C.; curve "+Enz (*3)": after 96 hours of incubation at 35° C. and addition of an additional volume of enzyme.

EXAMPLES

Example 1

Introduction

The objective of the Inventors has been to identify and to purify a sulfatase capable of partially or completely converting iota-carrageenan into alpha-carrageenan.

To this end, the Inventors have, firstly, developed a protocol to cultivate the bacterial strain *Pseudoalteromonas carrageenovora* 9 (ATCC 43555). This marine bacterium is in fact known to degrade certain polysaccharides extracted from red algae: carrageenans. Several carrageenan hydrolases, or carrageenases, derived from this bacterium have been identified and characterised in the laboratory. After a screening of the sulfatase activity under different experimental conditions, the Inventors have then developed a protocol for purifying to homogeneity the enzyme capable of desulfating iota-carrageenan into alpha-carrageenan.

Example 2

Materials and methods 2.1 Dosage and Identification of the Sulfatase Activity:
a) Desulfation Reaction 1 volume of sample (200 to 500 µl) to be assayed is incubated with 1 volume of iota-carrageenan (CP Kelco, Cargill) at a concentration of 1.4 in water. For each enzymatic reaction, a blank is prepared under similar conditions but by using the enzymatic extract inactivated beforehand through boiling for at least 10 minutes at 100° C.

After 15 to 20 hours of incubation at a temperature comprised between 25 and 37° C., the reaction mixture is diluted 2 times in milliQ water (Millipore) before being centrifuged in Microcons 10 (Amicon). The centrifugation is carried out at 3300 g for 60 to 90 minutes at a temperature comprised between 20 and 40° C.

b) Dosage of the Sulfate Released

The quantity of sulfate present in the filtrate is then dosed by ion exchange chromatography (HPAEC: high performance anion exchange chromatography) using a Dionex DX 500 system
(Dionex Corporation, Sunnyvale, Calif., USA). The separation of the anions present in the sample is carried out using an Ion-Pac AS11 type column (4×200 mm; Dionex) equipped with an AG-11 type pre-column (4×50 mm, Dionex). The column and pre-column are equilibrated beforehand in 12 mM NaOH. The elution of the anions is carried out at a flow rate of 1 ml/min (GP40 pump, Dionex). The detection of anions is carried out by conductimetry with an ED40 detector (Dionex) equipped with an ASRSD ultra-II-4 mm suppressor (Dionex) operating under a current of 100 mA.

c) Proton NMR Analysis

The identification of the product formed during the desulfation reaction is performed by NMR. In this case, the desulfation reaction is carried out by incubating 1 ml of sample with 500 µl of a 1.2 solution in water of iota-carrageenan (X-6908; CP-Kelco). The mixture is incubated for at least 16 hours at 35° C. The blanks are produced in a similar manner but with samples inactivated for 30 minutes at 100° C. before incubation at 35° C. After incubation, the samples are lyophilised then exchanged in deuterated water ($D_2O$, 2 exchange/lyophilisation cycles) before being analyzed by NMR (NMR Service of the Université de Bretagne Occidentale, Brest, N. Kervarec) (see point 3.2.c) below).

2.2 Bacterial Culture:

For a preliminary screening of sulfatase activity, the bacterial strain *Pseudoalteromonas carrageenovora* 9 of the American Type Culture Collection (ATCC 43555) is seeded in a ZoBell medium. The composition of the ZoBell medium is the following:

| | |
|---|---|
| Bacto peptone (Difco) | 5 g |
| Yeast extract (Difco) | 1 g |
| Filtered sea water | 800 ml |
| Water purified by reverse osmosis | 200 ml |

In order to potentially induce a sulfatase activity, the bacterial cultures (5×1000 ml) are carried out in the presence of different carrageenans (1 g/l) in a New Brunswick type agitator under an agitation comprised between 150 and 200 rpm.

After 36-40 hours of incubation at a temperature comprised between 15 and 20° C., the culture medium is centrifuged between 7500 and 9800 g for 30-60 minutes. The enzymatic activity is measured on the supernatant and on the culture pellet. Before testing its activity, the culture supernatant is concentrated beforehand by ultrafiltration on a membrane, the exclusion threshold of which is 10 kD. The filtrate obtained, the volume of which is around 200 to 300 ml, is further concentrated by precipitation to saturation in ammonium sulfate (65 g of ammonium sulfate/100 ml of sample). After centrifugation, the pellet obtained is re-suspended in a minimum volume of 50 mM Tris HCl buffer pH 8.3 and dialysed at least 72 hours against this buffer.

The culture pellet is re-suspended for around 1 hour in 30 to 50 ml of 50 mM Tris (Sigma) HCl buffer pH 8.3. The cells are then lysed using a French press. A centrifugation at 25-29000 g for 40 to 60 minutes is carried out to eliminate cell debris.

For the production of 4S-carrageenan sulfatases, the cultures (5×1 L) are carried out under similar conditions but the induction of the production of sulfatase is carried out in the presence of lambda carrageenan (1 g/l) (see point 3.1 below).

2.3 Purification of the Sulfatase

Unless otherwise indicated, all of the steps described in this paragraph are carried out at 4° C.

At the end of culture, the culture medium is centrifuged for 30-60 minutes between 7500 and 9800 g. The pellet obtained is re-suspended in 30 to 50 ml of 50 mM Tris (Sigma) HCl buffer pH 8.3. A pastille of Complete EDTA-free (Roche) is added. The cells are lysed with a French press (Aminco). After centrifugation, the supernatant thereby obtained is then brought to 30% saturation (16.4 g/100 ml) of ammonium sulfate. After centrifugation (25 to 29000 g; 40 to 60 min.), the supernatant is then deposited on a phenyl sepharose 6 FF high sub resin (GE Healthcare) (19.5×2 cm) equilibrated beforehand in 50 mM Tris HCl buffer (pH 8.3) saturated with 30% ammonium sulfate (16.4 q/100 ml). The resin is washed with this buffer until absorbance at 280 nm is negligible. The proteins are then eluted with a decreasing gradient of ammonium sulfate. In 20 volumes of column, the saturation in ammonium sulfate goes from 30% to 0%. The fractions (6.5 ml) capable of desulfating iota-carrageenan are collected together and dialysed using SpectraPor membranes, the cut-off of which is 3500 Daltons. The dialysis is conducted in a 50 mM Tris HCl buffer (pH 8.3).

The sample is then deposited on an ion exchange resin of DEAF sepharose FF type (GE Healthcare) (13×1.6 cm) equilibrated beforehand in 50 mM Tris HCl buffer (pH 8.3). After washing of the resin with this same buffer, the proteins are eluted with an increasing gradient of NaCl. The final concentration of 1M in NaCl is attained in 20 volumes of column. The different fractions collected during the elution (vol.: 5.5 ml) are tested for their ability to desulfate iota carrageenan. The degree of purity of the different fractions is also analyzed by electrophoresis on polyacrylamide gel (SDS-PAGE) (Laemmli and Favre, (1973) J. Biol. Chem. 80, 575-599).

Example 3

Results and Discussion 3.1 Bacterial Culture:
Screening of the Sulfatase Activity As shown in table 3 below, the presence of iota-, lambda- or nu-carrageenan in the culture medium induces, to various degrees, the production of sulfatase active on iota- and nu-carrageenan.

TABLE 3

Sulfatase activity in the supernatants and culture pellets after induction with iota-, nu- or lambda-carrageenan.

| Culture induced with | Sulfatase activity on Iota-carrageenan | Sulfatase activity on Iota/Nu-carrageenan |
|---|---|---|
| Iota carrageenan | | |
| Culture supernatant | + | − |
| Culture pellet | + | + |
| Lambda-carrageenan | | |
| Culture supernatant | − | − |
| Culture pellet | +++ | ++ |
| Nu-carrageenan | | |
| Culture supernatant | ++ | − |
| Culture pellet | ++ | ++ |

For an optimal production of enzyme, it may be observed that it is lambda carrageenan that turns out to be the most efficient. Indeed, the activity observed with this carrageenan is around 3 times greater than that observed when iota-carrageenan is used as inducer.

3.2 Purification and Characterisation of 4S-Iota-Sulfatase
a) Purification

Hydrophobic interaction chromatography (i.e. phenyl sepharose) is an important step because it makes it possible to eliminate a large part of the other proteins present in the bacterial pellet. Indeed, the sulfatase is eluted between 17 and 15% of saturation in ammonium sulfate whereas the other proteins are eluted when the concentration in ammonium sulfate is inferior to these values, or even nul.

All of the fractions that exhibit a sulfatase activity on iota carrageenan are collected together and dialysed for at least 72 hours. The dialysed sample (around 140 ml) is then purified by chromatography on an ion exchange resin. The measurement of the enzymatic activity of the different fractions collected (80) shows that the sulfatase is eluted when the concentration of NaCl is comprised between 300 and 430 mM. The maximum sulfatase activity is in fact observed in the sulfatase fractions that are eluted with an NaCl concentration comprised between 340 and 370 mM. Electrophoretic analysis under denaturing conditions of these fractions shows that the 4S-iota-carrageenan sulfatase is in the form of a unique protein, the molecular weight of which is around 110 kD (see FIG. 1).

b) Determination of the Peptide Sequence

In order to determine the peptide sequence of the sulfatase, the band corresponding to the protein was cut and subjected to trypsic digestion. The peptides obtained were purified and analysed by mass spectrometry on the R10 "Biopolymers" platform located at INRA in Nantes. The LC-MS/MS data compared with the TrEMBL databank showed a very large homology of sequence with the protein Q3IKL4 of *P. haloplanktis* (see FIG. 2). This sequence was then used to create a databank with which the MALDI data was compared to: Most of the major peptides (except 5) of the MALDI spectrum were identified in this sequence. The peptides measured in LC-MS/MS and not identified in the sequence Q3IKL4 were sequenced by mass spectrometry ("de novo"): all of these fragments correspond to sequence pieces that are found in Q3IKL4 (with several differences which explain why these peptides have not been identified on the basis of mass and sequence information).

The protein sequence Q3IKL4 (SEQ ID No 5) corresponds to a hypothetical protein of the marine bacterium *Pseudoalteromonas haloplanktis*, the genome of which has been entirely sequenced. *P. haloplanktis* is phylogenetically close to *P. carrageenovora* which implies that these two bacteria share enzymatic activities and genes in common.

c) Analysis of the Product of the Desulfation Reaction
See the protocol in point 2.1.c) above FIG. 3 shows the proton spectrum recorded on the iota-carrageenan before (A) and after incubation (B and C) with the sulfatase. As shown in this figure, the enzyme is capable of progressively converting iota-carrageenan (characterized by a chemical shift at 5.32 ppm—curve A of FIG. 3) into alpha-carrageenan (characterized by a chemical shift at 5.25 ppm). The complete conversion (curve C of FIG. 3) is however very slow (96 hours) and requires the addition of a volume of enzyme. The 2D NMR technique (HMQC) made it possible to confirm that the product formed after 96 hours of incubation was alpha-carrageenan.

BIBLIOGRAPHIC REFERENCES

Falshaw et al., 1996, Carbohydrate Research, 285, 82-98
Michel et al., Appl Microbiol Biotechnol. 2006 June; 71(1): 23-33. Epub 2006 March 21. Review
Potin et al., Eur J. Biochem. 1991 Oct. 1; 201(1):241-7.
Zablackis and Santos, 1986, Botanica Marina, 29, 319-322

The invention claimed is:

1. An isolated polypeptide comprising an amino acid sequence having at least 98% amino acid sequence identity with an amino acid sequence selected from the group consisting of SEQ ID NO: 2 and SEQ ID NO: 4, said polypeptide having 4S-iota-carrageenan sulfatase activity.

2. A method for obtaining an isolated 4S-iota-carrageenan sulfatase comprising:
   a) culturing *Pseudoalteromonas haloplanktis* in a culture medium containing iota-carrageenan or an iota/nu-carrageenan mixture under culture conditions suitable to obtain in the culture medium a 4S-iota-carrageenan sulfatase comprising the amino acid sequence of SEQ ID NO: 2 or culturing *Pseudoalteromonas carrageenovora* deposited as ATCC 43555 in a culture medium containing lambda-carrageenan under culture conditions suitable to obtain in the culture medium a 4S-iota-carrageenan sulfatase comprising the amino acid sequence of SEQ ID NO: 4; and
   b) isolating the 4S-iota-carrageenan sulfatase from the culture medium of step (a).

3. The method according to claim 2, in which step (b) includes the following sub-steps:

(b1) centrifuging the culture medium obtained at step (a) to obtain a cell pellet, and
   (b2) obtaining the 4S-iota-carrageenan sulfatase from the cell pellet obtained at step (b1).

4. The method according to claim 2 which further comprises, after step (b), the following additional step:
   (c) measuring the activity of the isolated 4S-iota-carrageenan sulfatase.

5. A method for converting a composition containing iota-carrageenan and/or hybrid iota-carrageenan into a composition which contains alpha-carrageenan and/or hybrid alpha-carrageenan, comprising the following steps:
   (a) bringing together the composition containing iota-carrageenan and/or hybrid iota-carrageenan with a solution containing an isolated polypeptide comprising an amino acid sequence having at least 98% amino acid sequence identity with the amino acid sequence SEQ ID NO: 2 or the amino acid sequence SEQ ID NO: 4, said polypeptide having 4S-iota-carrageenan sulfatase activity, under suitable conditions for the conversion of iota-carrageenan and/or hybrid iota-carrageenan in the composition into alpha-carrageenan and/or hybrid alpha-carrageenan; and (b) optionally, recovering the composition containing the alpha-carrageenan and/or hybrid alpha-carrageenan obtained at step (a).

6. The method according to claim 5, wherein the isolated polypeptide comprises an amino acid sequence selected from the group consisting of SEQ ID NO: 2 and SEQ ID NO: 4.

7. The method according to claim 5, in which the composition containing iota-carrageenan and/or hybrid iota-carrageenan is obtained from red marine algae.

8. The method according to claim 5, in which the composition containing alpha-carrageenan and/or hybrid alpha-carrageenan is a texturizing agent.

9. The isolated polypeptide according to claim 1, wherein said polypeptide is encoded by a polynucleotide comprising a nucleotide sequence having at least 98% nucleotide sequence identity with the nucleotide sequence SEQ ID NO: 1 or the nucleotide sequence SEQ ID NO: 3.

10. The isolated polypeptide according to claim 9, wherein said polypeptide is encoded by a polynucleotide comprising the nucleotide sequence selected from the group consisting of SEQ ID NO:1 and SEQ ID NO:3.

11. A vector comprising an isolated polynucleotide encoding a polypeptide comprising an amino acid sequence having at least 98% amino acid sequence identity with an amino acid sequence selected from the group consisting of SEQ ID NO: 2 and SEQ ID NO: 4, said encoded polypeptide having 4S-iota-carrageenan sulfatase activity.

12. A host cell transformed with the vector according to claim 11.

13. A method for producing a polypeptide comprising the following steps:
   a) culturing in a suitable medium and culture conditions a population of host cells as defined in claim 12; and
   b) recovering a polypeptide thereby produced from the culture medium or the population of cultured host cells, wherein said polypeptide comprises an amino acid sequence having at least 98% amino acid sequence identity with an amino acid sequence selected from the group consisting of SEQ ID NO: 2 and SEQ ID NO: 4, and where said polypeptide has 4S-iota-carrageenan sulfatase activity.

\* \* \* \* \*